(12) United States Patent
Lill

(10) Patent No.: US 10,603,023 B2
(45) Date of Patent: *Mar. 31, 2020

(54) DEVICE FOR REDUCING THE RETRACTION OF A FASCIA OR A SOFT TISSUE MANTLE IN AN OPEN SOFT TISSUE DEFECT

(71) Applicant: Fasciotens GmbH, Essen (DE)

(72) Inventor: Gereon Lill, Köln (DE)

(73) Assignee: Fasciotens GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/042,259

(22) Filed: Jul. 23, 2018

(65) Prior Publication Data

US 2018/0338750 A1 Nov. 29, 2018

Related U.S. Application Data

(63) Continuation of application No. 15/302,679, filed as application No. PCT/EP2015/057495 on Apr. 7, 2015, now Pat. No. 10,123,790.

(30) Foreign Application Priority Data

Apr. 10, 2014 (DE) .................. 10 2014 206 959
May 26, 2014 (DE) .................. 10 2014 209 995

(51) Int. Cl.
*A61B 17/02* (2006.01)
*A61F 13/00* (2006.01)
(Continued)

(52) U.S. Cl.
CPC .............. *A61B 17/02* (2013.01); *A61B 17/08* (2013.01); *A61F 13/00068* (2013.01); *A61B 2017/00991* (2013.01); *A61B 2017/0287* (2013.01)

(58) Field of Classification Search
CPC ..... A61B 17/02; A61B 17/08; A61B 17/0206; A61B 17/0293; A61B 17/20;
(Continued)

(56) References Cited

U.S. PATENT DOCUMENTS 3,572,326 A * 3/1971 Jensen ............... A61B 17/0293
600/233
RE32,021 E * 11/1985 Scott, Jr. ............ A61B 17/0293
600/217
(Continued)

FOREIGN PATENT DOCUMENTS

DE          3444782 C2    3/1988
DE          3631762 A1    3/1988
(Continued)

OTHER PUBLICATIONS

International Search Report for International Application No. PCT/EP2015/057495 dated Jun. 8, 2015.
(Continued)

*Primary Examiner* — Pedro Philogene
(74) *Attorney, Agent, or Firm* — The Dobrusin Law Firm, P.C.

(57) ABSTRACT

The invention relates to a device for reducing the retraction of the edges (4.1) of an opened fascia (4) of a patient (1) having an open soft tissue defect, in particular having an open abdominal wall (2) or an open soft tissue defect on the back, via which a tensile force (A, B) can be applied to the edges (4.1) of the fascia (4) by a force component (A1, B1) directed away from the body of the patient (1), such that the device (11) holds the edges (4.1) of the fascia (4) under tension and spaced apart from each other and that furthermore there is an open soft tissue defect, in particular an opened abdominal wall (2), or an open soft tissue defect on the back. The invention further relates to a kit for treating an open soft tissue defect, in particular of an opened abdominal
(Continued)

wall (2) or of an open soft tissue defect on the back, having at least one sponge (9, 15, 28) for filling out an opening (7) of a soft tissue defect, in particular in the abdominal wall or of en open soft tissue defect on the back, and having such a device (11) for reducing the retraction of the edges (4.1) of an opened fascia (4).

17 Claims, 13 Drawing Sheets

(51) Int. Cl.
    *A61B 17/08*     (2006.01)
    *A61B 17/00*     (2006.01)

(58) Field of Classification Search
    CPC ............ A61B 17/0218; A61B 17/0243; A61B 17/085; A61B 2017/00991; A61B 2017/0287; A61B 2017/00473; A61B 2017/00752; A61B 2017/308; A61B 2017/00876; A61B 2017/0243; A61B 2090/064; A61B 2090/0807; A61B 90/02; A61B 90/50; A61B 34/30; C03B 23/0307; C03B 23/0302; C03C 21/002
    USPC .... 600/215, 201, 209, 227, 235; 606/133, 1, 606/187, 151, 213, 220, 215, 217
    See application file for complete search history.

(56) References Cited

U.S. PATENT DOCUMENTS

| | | | |
|---|---|---|---|
| 5,307,790 A | | 5/1994 | Byrne |
| 5,437,683 A | | 8/1995 | Neumann et al. |
| 5,782,746 A | * | 7/1998 | Wright ............... A61B 17/0206 128/897 |
| 5,876,333 A | * | 3/1999 | Bigliani ................. A61B 17/02 600/231 |
| 6,387,047 B1 | | 5/2002 | Duhaylongsod et al. |
| 10,123,790 B2 | * | 11/2018 | Lill ........................ A61B 17/02 |
| 2007/0156028 A1 | * | 7/2007 | Van Lue .................. A61B 1/24 600/237 |
| 2010/0191253 A1 | | 7/2010 | Oostman, Jr. et al. |
| 2012/0130180 A1 | | 5/2012 | Pell et al. |
| 2015/0011836 A1 | | 1/2015 | Foulon et al. |

FOREIGN PATENT DOCUMENTS

| | | |
|---|---|---|
| DE | 4034705 A1 | 5/1992 |
| DE | 112011102552 T5 | 5/2013 |
| JP | H0871073 A | 3/1996 |
| WO | 9406354 A1 | 3/1994 |
| WO | 2013092938 A1 | 6/2013 |

OTHER PUBLICATIONS

Fankhauser et al., "Sekundärverschluß von Hautdefekten unter Anwendung von Gummizügen (dynamische Sekundärnaht)" ["Secondary closure of skin defects using rubber cords (dynamic secondary seam)"], Chirurg (1995) 66, 1154-1157, ISSN 0009-4722.
Seternes A. et al.: Early Results after Treatment of Open Abdomen after Aortic Surgery with Mesh Traction and Vacuum-Assisted Wound Closure. European Journal of Vascular and Endovascular Surgery, vol. 40, Jul. 2010, 60-64.—ISSN 1078-5884. http://dx.doi.org/10.1016/j.ejvs.2010.02.018.

* cited by examiner

DEVICE FOR REDUCING THE RETRACTION OF A FASCIA OR A SOFT TISSUE MANTLE IN AN OPEN SOFT TISSUE DEFECT

FIELD OF THE INVENTION

The invention relates to an apparatus and a method for reducing the retraction of the edges of an open fascia of a patient with an open soft tissue defect, in particular with an open abdominal wall or an open soft tissue defect on the back. The invention also relates to a kit for treating an open soft tissue defect, in particular an opened abdominal wall or an open soft tissue defect on the back, having at least one sponge for filling a soft tissue defect, in particular an opening in the abdominal wall or an open soft tissue defect on the back.

A sponge for negative-pressure wound therapy is also described.

The invention may be used in the case of open soft tissue defects. Such soft tissue defects may exist for example in the form of an abdominal wall defect, a back wall defect, a soft tissue defect in the region of the hip, or a soft tissue defect on the limbs.

PRIOR ART

For the treatment of certain abdominal illnesses associated with an intra-abdominal pressure increase, an abdominal compartment syndrome, it may be necessary for the abdominal wall to be opened up in order to expose the abdominal cavity and counteract an increase of the intra-abdominal pressure. This state is also referred to as "open abdomen". Here, the abdominal wall remains widely opened normally for a period of several days up to a number of months. An open abdomen may also be necessary, or involved, in the case of other diagnoses without an intra-abdominal pressure increase.

In general, the abdominal wall is temporarily sealed off by way of a temporary abdominal closure in the form a vacuum bandage, such that negative-pressure wound therapy can be performed. Here, a sponge-like material is inserted into the gap in the abdominal wall, and the open abdomen is sealed off by way of films. By way of the sponge, a negative pressure is applied, and excess liquid is drawn out of the abdominal cavity. Alternatively, the wound may also be tended to without negative-pressure wound therapy.

Therapy by way of an open abdomen has proven to be particularly advantageous for the healing of illnesses of the abdominal cavity. Opening the abdominal wall however has the disadvantage that the edges of the opened fascia situated in the abdominal wall can retract in the direction of the sides while the abdomen is open for days or weeks. As a result, closing the abdominal wall and thus the fascia after normalization of the intra-abdominal pressure is made difficult or impossible. Primary wound healing, in the case of which the wound edges lie against one another, is often not possible. Even secondary wound closure by layers can often not be achieved. It may be the case that secondary wound healing occurs over a long period of time, which is associated with the formation of scar tissue. The wound often heals with an incisional hernia.

To bridge the time until permanent closure of the abdominal wall occurs, and to bring the edges of the fascia closer to one another, it is often the case after therapy by way of an open abdomen that the abdominal wall is closed only temporarily. For example, DE 36 31 762 A1 has disclosed a temporary closure for an abdominal wall opening, by way of which the abdominal wall can be temporarily closed and, in the process, a tension is exerted on the edges of the fascia. DE 4034 705 A1 discloses a further temporary closure in the case of which a tension is imparted to the edges of the open fascia. Furthermore, DE 34 44 782 C2 describes a sliding closure which can be sewn to the edges of the open fascia in order to close the latter.

In the case of the abovementioned temporary abdominal wall closures, the edges of the open fascia are placed under tension, such that subsequent permanent closure of the fascia by way of primary wound healing is made possible. In the case of these closures, the fascia edges are pulled toward one another so as to bear against one another. Since, in the case of these temporary closures, the abdominal cavity is not open, the abdominal organs of the patient cannot expand, which is however vital for patients with an increase in intra-abdominal pressure. It is often necessary, owing to the retracted fasciae after the in any case relatively long period of the abdomen being open, for the abdominal wall to remain only temporarily close for a relatively long period of time before the permanent closure of the abdominal wall can be performed. This is often realized only with the aid of alloplastic materials.

The publication "Sekundärverschluß von Hautdefekten unter Anwendung von Gummizügen (dynamische Sekundärnaht)" ["Secondary closure of skin defects using rubber cords (dynamic secondary seam)"], Fankhauser et al., Chirurg (1995) 66, 1154-1157, ISSN 0009-4722, discloses a secondary wound closure for a skin defect in the region of the limbs, in the case of which the skin edges are pulled toward one another by way of transcutaneously or intracutaneously fixed rubber cords. With this method, although it is possible to stretch the skin in order to permit a secondary closure of the skin, it is a disadvantage that reduction of the retraction of the fasciae lying under the skin, in particular while the fascia opening exists, cannot be achieved. A further disadvantage of said apparatus consists in that the apparatus is supported on the skin edges on which a pulling action is exerted, whereby the space situated under the skin defect is reduced in size.

The abovementioned disadvantages also arise in the case of other open soft tissue defects, such as for example an open back wall or an open soft tissue defect in the region of the hip or on the limbs. In the region of the back, it may for example be necessary after an operation for the back wall to be left open for treatment of infections, wherein a retraction of the fasciae may likewise occur.

DISCLOSURE OF THE INVENTION

Against this background, it is the object of the invention to permit the permanent closure of the soft tissue defect, in particular of the abdominal wall or of the back wall, immediately after therapy with an open soft tissue defect, in particular with an open abdomen or an open back wall.

The object is achieved by way of an apparatus for reducing the retraction of the edges of an open fascia of a patient with an open soft tissue defect, in particular with an open abdominal wall or an open soft tissue defect on the back, by way of which apparatus a tensile force with a force component directed away from the body of the patient can be exerted on the edges of the fascia such that the apparatus holds the edges of the fascia under tension and spaced apart from one another and such that an open soft tissue defect, in particular an opened abdominal wall or an open soft tissue defect on the back, remains present.

By way of the tensile force acting on the fascia, the edges of the opened fascia are held spaced apart, such that access to the body cavity situated under the soft tissue defect, in particular to the abdominal cavity, is possible, negative-pressure wound therapy, for example, can be performed, or the abdominal organs can expand through the soft tissue, defect, in particular the abdominal wall opening or a soft tissue defect on the back. Furthermore, by way of the tensile force, the tension of the fascia is maintained, and thus the retraction of the edges of the fascia is at least reduced. After the completion of the therapy by way of an open soft tissue defect, in particular by way of an open abdomen or open soft tissue defect on the back, the edges of the fascia can be laid against one another and directly closed, whereby improved wound healing with permanent closure of the soft tissue, in particular of the abdominal wall or of the back wall, is made possible.

By way of the apparatus according to the invention, the fascia can be held open to such an extent that the body cavity situated under the soft tissue defect, in particular the abdominal cavity, is freely accessible, and/or the internal organs can emerge at least substantially unhindered through the skin defect, in particular the abdominal wall opening or the back wall opening. This yields the advantage that an unhindered release of an excess pressure in the body, in particular in the abdominal cavity or in the cavity below the back wall, or the unhindered escape of excess fluid from the body, in particular from the abdominal cavity of the cavity below the back wall, is possible. According to the invention, the edges of the opened fascia are held by way of the tensile force so as not to lie against one another. The apparatus is preferably designed such that no connecting means arranged in the plane of the body surface, in particular of the abdominal wall or back wall, is arranged between the fascia edges.

The apparatus according to the invention permits an increase in volume of the body cavity originally situated under the soft tissue defect by way of an expansion into the space originally occupied by the soft tissue.

It is particularly preferably the case that the tensile force imparted by way of the apparatus is oriented such that the edges of the opened fascia are not pulled toward one another. In this respect, the tensile force is preferably exerted on the edges of the fascia such that the open soft tissue defect is not reduced in size. The tensile force is advantageously oriented such that the space bordered by the edges of the fascia is increased in size.

The apparatus may be designed such that the tensile force engages on the fascia of the abdomen substantially in a ventral direction or in a ventrolateral direction or in a lateral direction. Alternatively, the apparatus may be designed such that the tensile force engages on the fascia of the back in a dorsal direction or dorsolateral direction. It is preferably the case that at least one component of the tensile force is oriented transversely, in particular perpendicular, to a virtual connecting line between the edges of the body opening, in particular opened abdominal wall or opened back wall, or of the opened fascia. The tensile force acting on the edges of the fascia thus has a component running away from the patient transversely, in particular perpendicularly, to the body opening, in particular abdominal wall opening or back wall opening. The edge of the fascia may however also be folded over and then held under tension. In this case, the tensile force is directed substantially parallel to the body surface, in particular to the abdominal wall or back wall, of the patient but away from the body opening, in particular the abdominal wall opening or back wall opening.

In one advantageous refinement, the apparatus is designed such that the tensile force engages on the fascia in a direction which encloses an angle in the range of 5° to 90°, or in the range of 10° to 80° or in the range of 15° to 70°, with a virtual connecting line between the edges of the opened fascia. The angle preferably lies in the range from 30° to 60°, particularly preferably in the range from 35° to 55°. The angle may for example amount to substantially 45°.

It is advantageous if the apparatus has at least one tensile element that can be connected to the fascia. The tensile force can be introduced into the fascia by way of the tensile element. It is preferable for multiple tensile elements to be provided by way of which tensile forces can be exerted on the edges of the opened fascia at several different points. The various tensile elements may in each case introduce tensile forces of different magnitude and different orientation into the fascia. Alternatively, the tensile element may be connected to the body surface, in particular to the abdominal wall or back wall, including the fascia, such that not only the fascia but also the skin lying over the fascia is held under tension.

The tensile element is preferably in the form of a thread and/or in the form of a wire and/or in the form of a mesh. Use may be made of conventional threads, wires or meshes that are used in surgery. It is particularly advantageous if the tensile element has a spring means which can be preloaded in the direction of the tensile force, such that the tensile element can be held under stress. Alternatively or in addition, the tensile element may be of elastic form and preloaded in the direction of the tensile force. The tensile element may be attached to the fascia directly or indirectly by way of a connecting means. The tensile element is preferably in the form of a combination of a thread and/or of a wire and/or of a mesh.

It is also preferable if the tensile element can be connected to the fascia by way of a connecting means of an areal form. By way of the aerial connecting means, an improved attachment of the tensile element to the fascia, can be realized. The risk of the fascia being torn out can be reduced, and the fascia can be protected in the case of repeated exchange of the tensile element. A refinement is particularly preferable in which the areal connecting means can be sewn to the fascia. Alternatively, the connecting means may for example have hooks, in particular barbs, which can be introduced into the fascia. The connecting means may for example be in the form of a mesh or in the form of a plate. The tensile element may be connectable by way of the connecting means of areal form to the fascia and additionally to other constituent parts of the soft tissue mantle, preferably to the entire soft tissue mantle. For example, aside from the fascia, the skin may also be connected to the areal connecting means.

It is advantageous if the connecting means of areal form can be connected reversibly to the tensile element, such that the tensile element and/or the mounting bracket can be easily removed and attached again for the purposes of treating the open soft tissue defect, in particular the open abdomen or the open back.

The apparatus advantageously has a mounting bracket which can be arranged outside the body of the patient and to which the tensile element can be attached. The mounting, bracket may be positioned in front of the soft tissue defect, in particular the abdominal wall opening or back wall opening, of the patient. It is possible for one end of the tensile element to be attached to the mounting bracket, and for the other end of the tensile element to be attached to the fascia. It is alternatively possible for both ends of the tensile element to be attached to the fascia and for the tensile element to be guided over a diverting device arranged on the mounting bracket. The two ends of the tensile element may be attached to the same edge section of the opened fascia or to different edge sections of the opened fascia.

In one advantageous refinement, the tensile elements are attached to the mounting bracket such that a tensile force is exerted on the edges of the fascia by way of the tensile elements, which tensile force acts in a direction which encloses an angle which lies in the range from 5° to 90° or in the range from 10° to 8°, or in the range from 15° to 70°, with a virtual connecting line between the edges of the opened fascia. The angle preferably lies in the range from 30° to 60°, particularly preferably in the range from 35° to 55°. The angle may for example amount to substantially 45°.

It has also proven to be advantageous if the tensile force can be adjusted by way of a tensioning apparatus arranged in particular on the mounting bracket. The tensioning apparatus may be manually actuable, such that the tension of individual tensile elements or the tension of a group of tensile elements can be adjusted while the soft tissue defect, in particular the opened abdomen or the opened back wall, exists. It is thus possible to react to changes of the fascia, and to adjust the tension if necessary. Alternatively, the tensioning apparatus may be designed so as to automatically re-tension the tensile element as soon as a relaxation of the tensile element occurs. The tensioning apparatus may have a force booster, for example a lever-type force booster, such that the tensile force can be adjusted by way of an adjustment force which is lower than the tensile force.

The tensioning apparatus is preferably designed such that the tensile force acting on the fascia can be adjusted without the tensile element being released from the fascia and/or from the mounting bracket. It is advantageous if each tensile element is assigned a dedicated tensioning apparatus such that the tension of the tensile elements can be individually set. Alternatively or in addition, a tensioning apparatus may be assigned to a group of tensile elements, such that the stress of the tensile elements of the group can be adjusted jointly.

It is also advantageous if the apparatus has a protective apparatus which, in the event of a predefined tensile force being exceeded, places a tensile element or multiple tensile elements into a protective state in which the tensile force exerted on the fascia by way of the tensile element is reduced. This yields the advantage that the fascia can be protected against the exertion of excessively high tensile forces. In the protective state, the tensile element may be released from the fascia and/or from the mounting bracket. It is furthermore possible for the tensile element to be relaxed in the protective state.

A preferred refinement provides that the mounting bracket can be arranged so as to run vertically, that is to say parallel to an imaginary line between the head and feet of the patient, along the abdomen or along the back. The mounting bracket may be arranged from the region of the sternum into the region of the anterior pelvic ring, such that a mounting bracket running craniocaudally is formed. The mounting bracket may have one or more, in particular vertically running, rods. It is alternatively possible for the mounting bracket to be formed in the manner of a frame which can be arranged around the soft tissue defect, in particular around the opening of the abdominal wall. In the case of a mounting bracket with rods, the rods preferably run in straight or curved fashion. The rods advantageously have a polygonal or circular cross section.

The mounting bracket can preferably be attached to the body of the patient, such that, when the patient changes position, the mounting bracket can move together with the patient. The attachment may be realized by way of a fastening device, in particular a strap-type fastener or a fastening chain, which can be fixed to the body of the patient. It is possible for multiple fastening devices to be provided. An embodiment is preferable which has two fastening devices which can be arranged in the upper (cranial) and lower (caudal) region of the abdomen or of the back.

The fastening device is preferably designed such that it can be applied to the skin of the patient or can be fastened to a bone of the patient. The fastening may be realized for example to the sternum and/or to the anterior pelvic ring. For the fastening of the fastening device to a bone, the fastening device may preferably be fixed in the bone, for example by virtue of the fastening device, and/or a connecting means connected to the fastening device, being screwed or pushed or driven into the bone.

An advantageous refinement provides that the fastening device is designed as a corset which can be fixed to the body of the patient.

The fastening device of the apparatus is preferably provided such that said fastening device can be applied to the skin in a region surrounding the soft tissue detect, in which region no tensile forces are exerted by the apparatus on the fascia lying under the skin.

A further preferred refinement provides that the fastening device has a pressure-distributing means that can be applied to the skin of the patient. The pressure-distributing means can preferably be filled with a medium. As a medium for filling the pressure-distributing means, use may be made of a gas, in particular air, a liquid, in particular water, or a gel. The pressure-distributing means may have a chamber into which the medium can be introduced. By way of the pressure-distributing means, pressure forces acting on the skin of the patient can be distributed uniformly, such that the risk of the formation of pressure points on the skin is reduced. The fastening device particularly preferably has a pressure-distributing means with multiple, in particular two, chambers. It is advantageous if the chambers are designed such that they can be alternately filled with a medium such that the pressure forces can be introduced alternately into different regions of the skin. The chambers are preferably formed in the manner of concentric circles, wherein a first chamber is in the form of a circular ring which surrounds a second chamber.

In a preferred refinement, the fastening device has an implant which can be fastened to a bone of the patient. The implant may be formed as an internal fixator. The implant is particularly preferably an implant that is already present in the body of the patient, such as for example a spinal column implant. It is alternatively possible for the implant to be introduced together with the apparatus for reducing the retraction of the fasciae. The implant may have one or more longitudinal members. The longitudinal members of the implant may be fastenable to bones of the patient, for example to vertebrae of the spinal column. For the fastening of the implant, in particular of the longitudinal members, to the bones, the implant preferably comprises one or more connecting means, in particular one or more screws.

A preferred refinement provides that the apparatus has a force measurement device for the measurement of the tensile force exerted on the fascia by the tensile element. The force measurement device may be designed such that the sum of the tensile forces exerted by the various tensile elements can be measured. The apparatus particularly preferably has multiple force measurement devices for the measurement of the tensile forces exerted by the various tensile elements. The force measurement device may be designed such that the tensile force exerted by one tensile element, or the tensile force exerted by a group of tensile elements, can be measured in each case. The force measurement device may have a spring force sensor, an inductive force sensor, a capacitive force sensor, an optical force sensor, a strain gauge, a magnetic force sensor, an electromagnetic force sensor or a piezoelectric force sensor. The force measurement device may be connected to a tensile element, in particular such that the force measurement device is arranged in the force flow of the tensile force. Alternatively or in addition, the force measurement device may be arranged between the mounting bracket and the fastening device, in particular in a strut provided between the mounting bracket and the fastening device. It is furthermore possible for the force measurement device to be formed as part of the fastening device, which has a pressure-distributing means that can be filled with a medium, for example a gel. Through measurement of the compression of the medium, the force exerted on the pressure-distributing means can be determined.

The fastening device is particularly preferably designed such that it can be sewn to the tissue, in particular the skin, of the patient.

It is advantageous if the mounting bracket can be attached to the body of the patient by way of multiple fastening devices, wherein the fastening devices are of different design. For example, a fastening device in the form of a strap-type fastener may be used in the upper region of the abdomen or of the thorax, and a fastening device that can be fastened to a bone of the patient may be used in the lower region of the abdomen. Alternatively, the fastening devices may be of identical design. For example, two fastening devices in the form of strap-type fasteners may be provided, in particular a first fastening device in the upper region of the abdomen or of the thorax and a second fastening device in the lower region of the abdomen. A further alternative consists in that only a single fastening device is provided. It may be provided that the single fastening device can be arranged either in the upper region of the abdomen or of the back or in the lower region of the abdomen or of the back.

A particularly advantageous refinement provides that the mounting bracket is mounted so as to be movable, in particular movable in pivotable fashion, relative to the fastening device. By way of such a mounting, movements of the patient that may arise for example as a result of respiration and/or coughing can be compensated. The mounting bracket may preferably be entirely arranged so as to be movable relative to the patient. Alternatively, the mounting bracket may be rigidly coupled to and/or formed in one piece with the fastening device.

The mounting bracket may be coupled for example to the fastening device by way of at least one joint, which is advantageously in the form of a rotary joint or in the form of a ball joint. It is possible for multiple joints to be provided on the mounting bracket, such that the mounting bracket can move relative to multiple fastening devices. In the case of a mounting bracket formed in the manner of a frame with multiple frame sections, the frame sections may be connected to one another by way of joints in order to permit movements of the frame sections relative to one another. Alternatively, the mounting bracket may be coupled to the fastening device by way of spring elements, for example by way of resilient telescopic rods.

The mounting bracket is preferably connected in non-positively locking fashion to the fastening device.

It is also preferable if the mounting bracket can be adapted to the body of the patient, such that the apparatus can be used for patients of different physical build. The mounting bracket may be of telescopable form and/or designed to be assemblable from multiple modules, such that the dimensions of the mounting bracket can be adjusted in accordance with the physical build of the patient.

In this context, it is particularly preferable if the length of the mounting bracket, in particular in a direction running vertically along the abdomen or the back, is adjustable. The length of the mounting bracket can be adjusted for example by way of a telescopable element, in particular a telescopic rod. The telescopic rod may have a detent device by way of which the length of the telescopic rod can be fixed.

It is furthermore advantageous if the position of the mounting bracket relative to the body can be adjusted. For variation of the position of the mounting bracket, use may be made of a telescopable element.

As an alternative to an attachment of the mounting bracket to the patient, the mounting bracket may be attachable to a holder which is independent of the patient, in particular to a bed or to a stretcher or to a holder that is supported on the ground. In the case of attachment to a holder which is independent of the patient, it must be ensured that, when the patient changes position, the mounting bracket can be moved together with the patient in order to be able to maintain the tensile force on the fascia unchanged.

The mounting bracket is preferably selectively attachable either to the patient or to a holder which is independent of the patient, in particular to a bed or to a stretcher, such that a switch can be made back and forth between said two types of mounting bracket as required, or both types of mounting bracket may be utilized simultaneously. The holder which is independent of the patient is particularly preferably in the form of a boom extension, a bed mounting point attached to a bed, or a holder that is supported on the ground.

To achieve the object mentioned in the introduction, a sponge for negative-pressure wound therapy is also proposed, which sponge has a substantially triangular or substantially trapezoidal or substantially semicircular or substantially semioval or substantially semielliptical cross section. Alternatively, the sponge may have a rectangular cross section with a ratio of height to width in the range from 1/1 to 1/5. The sponge is preferably designed so as to fill a region between the edges of an open fascia and an apparatus, which acts on the fascia, for reducing the retraction of the edges of an open fascia.

In a preferred refinement, the sponge has an internally situated region with increased strength in relation to its surface, or has an internally situated, non-deformable basic shape. This yields the advantage that the sponge exhibits increased stability.

To achieve the object mentioned in the introduction, a sponge for negative-pressure wound therapy is also proposed, which sponge has a recess for receiving an in particular elongate object, for example a mounting bracket, and/or the contour of which sponge is adapted to the outer contour of the mounting bracket. The mounting bracket of the above-described apparatus can be covered by way of the sponge, such that sealing can subsequently be performed by way of a sealing means, for example a film. The sponge may have a cross section which substantially has the shape of a sector of a circular ring.

In the case of a kit of the type mentioned in the introduction, it is proposed, for the purposes of achieving the object, that an above-described apparatus for reducing the retraction of the edges of an opened fascia of a patient be provided.

The same advantages as those already described in on with the apparatus according to the invention for reducing the retraction of the edges of an opened fascia of a patient can be achieved in this way.

An advantageous refinement of the kit provides that the kit additionally has a sealing means for sealing off the open soft tissue defect, in particular the abdomen or the open back. The sealing means may be in the form of a film which, on that side of the sponge which is averted from the body, can be applied, in particular adhesively bonded, to the open soft tissue defect, in particular the opened abdominal wall or the open back wall. By way of the sealing means, the body cavity, in particular the abdominal cavity or the cavity situated within the back wall, can be closed off in liquid-tight and gas-tight fashion. The sealing means may be arranged such that the apparatus for reducing the retraction of the edges of an opened fascia is situated entirely or partially within the region sealed off by the sealing means. The sealing means is preferably in the form of a non-adhesive film that is impermeable to air. The non-adhesive film that is impermeable to air may lie directly on the apparatus for reducing the retraction of the fascia edges. The non-adhesive, air-impermeable film may be fixed to the body of the patient by way of adhesive means, for example an adhesive film. The sealing means advantageously has one or more, for example two, openings, through which a part of the apparatus for reducing the retraction of the fascia edges, for example a mounting bracket, can be led. In the region of the opening there may be provided a sealing element, for example a ring-shaped and/or adhesive sealing element or a sealing element in the form of a tensile device, by way of which the non-adhesive, air-impermeable film can be brought into sealing contact with the apparatus.

The kit preferably has a vacuum pump for generating a negative pressure in the body cavity, in particular in the abdominal cavity or in the cavity situated within the back wall, of the patient. By way of the vacuum pump, excess liquids and/or gases can be suctioned out of the body cavity, in particular the abdominal cavity or the cavity situated within the back wall.

It is advantageous if the apparatus for reducing the retraction of the edges of the opened fascia has a mounting bracket which can be arranged outside the body of the patient and to which there can be attached a tensile element which can be connected to the fascia, and the kit has a sponge, the contour of which is adapted to the outer contour of the mounting bracket.

The features described in conjunction with the apparatus according to the invention may be used individually or in combination in the case of the kit.

The achievement of the object mentioned in the introduction is furthermore contributed to by a method for reducing the retraction of the edges of an open fascia of a patient with an open soft tissue defect, in particular with an open abdominal wall or an open soft tissue defect on the back, wherein a tensile force with a force component directed away from the body of the patient is exerted on the edges of the fascia such that the edges of the fascia are held under tension and spaced apart from one another and such that an open soft tissue defect, in particular an opened abdominal wall or an open soft tissue defect on the back, remains present.

The method can be performed without the soft tissue detect, in particular on the abdomen or on the back, being treated simultaneously by way of negative-pressure wound therapy. The method is preferably carried out on a soft tissue defect, in particular on the abdomen or back, which is simultaneously being treated by way of negative-pressure wound therapy.

The features described in conjunction with the apparatus according to the invention and the kit may be used individually or in combination in the case of the method.

BRIEF DESCRIPTION OF THE DRAWINGS

Further advantages and details of the invention will be described below on basis of the exemplary embodiments illustrated in the figures, in which.

EXEMPLARY EMBODIMENTS OF THE INVENTION

Figure 1:
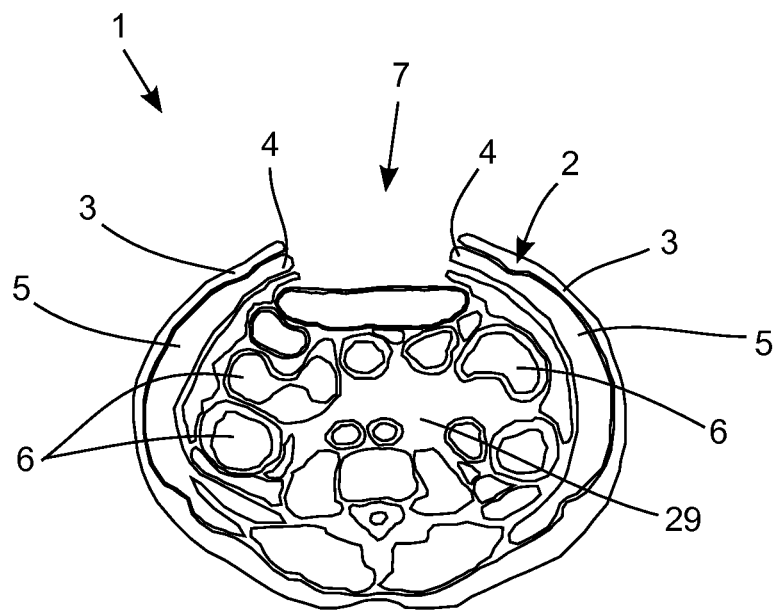
FIG. 1 is a schematic sectional illustration of a human abdomen along a transverse plane in the case of an opened abdomen.

FIG. 1 illustrates a transverse section through an open human abdomen. The abdominal wall 2 is composed substantially of the skin 3, of the abdominal muscle 5 situated under the skin 3, and of the fasciae 4. Between the skin 3 and the abdominal muscle 5 there is arranged subcutaneous tissue (not illustrated in the figures). The fasciae 4 are of great importance for the stability of the abdominal wall 2. The fasciae 4 enclose the abdominal muscle 5 and lie against that side of the skin 3 which faces toward the abdominal cavity 29.

In the case of some disease patterns which are associated with an intra-abdominal pressure increase, an abdominal compartment syndrome, it may be necessary to lower the pressure by opening up the abdominal wall 2 of the patient 1 and removing excess gases and/or liquids from the abdominal cavity 29 through abdominal wall opening 7 created by surgical measures. Here, it may be the case that internal organs, for example the intestines 6, emerge through the abdominal wall opening 7.

Figure 2:
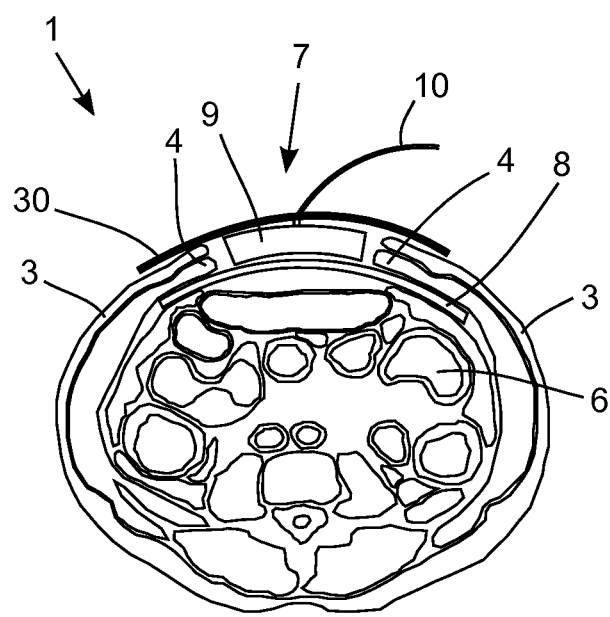
FIG. 2 is a schematic sectional illustration of a human abdomen along a transverse plane with a temporary abdominal wall closure according to the prior art during performance of negative-pressure wound therapy.

To counteract the occurrence of infections in the abdominal cavity 29 and to facilitate the care of the open abdomen, the abdominal wall opening 7 is generally temporarily sealed off, and negative-pressure therapy is simultaneously performed. As can be seen from the illustration an FIG. 2, it is the case here that the abdominal cavity 29 is covered for example by way of a sponge 8 arranged below the abdominal wall 2. Between the sponge 8 and the intestines 6 there is preferably arranged a film (not illustrated in the figures) or a separating material for preventing the intestine 6 from drying out. A preferably further sponge 9 is introduced into the abdominal wall opening 7, and the abdominal wall opening 7, is sealed off by way of a sealing means 30, which is normally in the form of a gas-tight adhesive film. The sponge 9 is connected by way of a suction hose 10 to a vacuum pump. By way of the vacuum pump, a negative pressure is applied such that undesired liquids and/or gases can be removed from the abdominal cavity 29 through the suction hose 10. Said negative-pressure therapy is generally performed over a duration of several days up to several weeks. A person skilled in the art understands that the abdominal wall opening 7 may also be covered in some other way.

Figure 3:
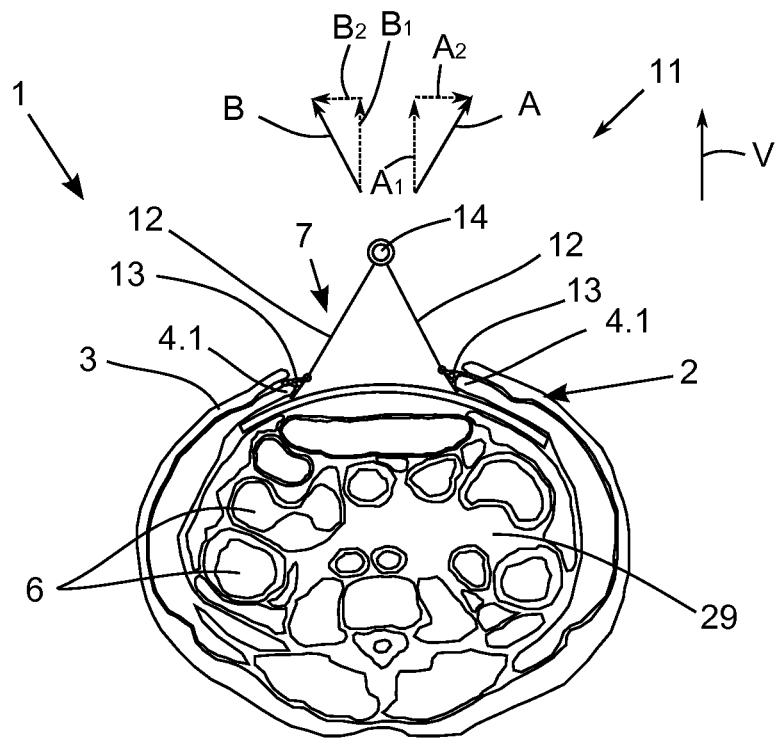
FIG. 3 is a schematic sectional illustration of a human abdomen along a transverse plane with an apparatus according to the invention for reducing the retraction of an opened fascia as per a first exemplary embodiment of the invention.

In order that the edges 4.1 of the fascia 4 do not unduly retract during said time period, and the closure of the fascia 4, that is to say the connection of the fascia edges 4.1, is possible with non-problematic wound healing after the period of the abdomen being open, an apparatus 11 according to the invention for reducing the retraction of the fascia 4 is inserted after the abdominal wall 2 is opened, of, FIG. 3.

As can be seen from the illustration in FIG. 3, by way of the apparatus 11 according to the invention, tensile forces A, B with a force component $A_1$, $B_1$ directed away from the body of the patient 1 are exerted on the edges 4.1 of the fascia 4 such that the apparatus holds the edges 4.1 under tension and spaced apart from one another. The abdominal wall 2, and thus also the fascia 4, is held open. The abdominal wall opening 7 has an extent of greater than 1 cm, preferably of greater than 5 cm, such that unhindered access to the abdominal cavity 29 is possible.

The apparatus 11 preferably has multiple tensile elements 12 by way of which the tensile forces A, B are introduced into the fascia edges 4.1. The tensile elements 12 are preferably in the form of threads. Use may alternatively be made of wires, cables or meshes. The tensile elements 12 may be of elastic or non-elastic form. It is basically possible for the tensile elements 12 to be connected directly to the fascia 4. To prevent the tensile elements 12 from being torn out, and to prevent damage to the fascia 4, the tensile elements 12 are preferably connected to the fascia by way of an areal connecting means 13 in the form of a mesh. The areal connecting means 13 can distribute the considerable tensile forces over a relatively large area, and thus improve the introduction into the fascia 4. The mesh may remain connected to the fascia 4 throughout the entire duration of the treatment of the open abdomen. The tensile elements 12 may however be exchanged as required.

Figures 5, 6:
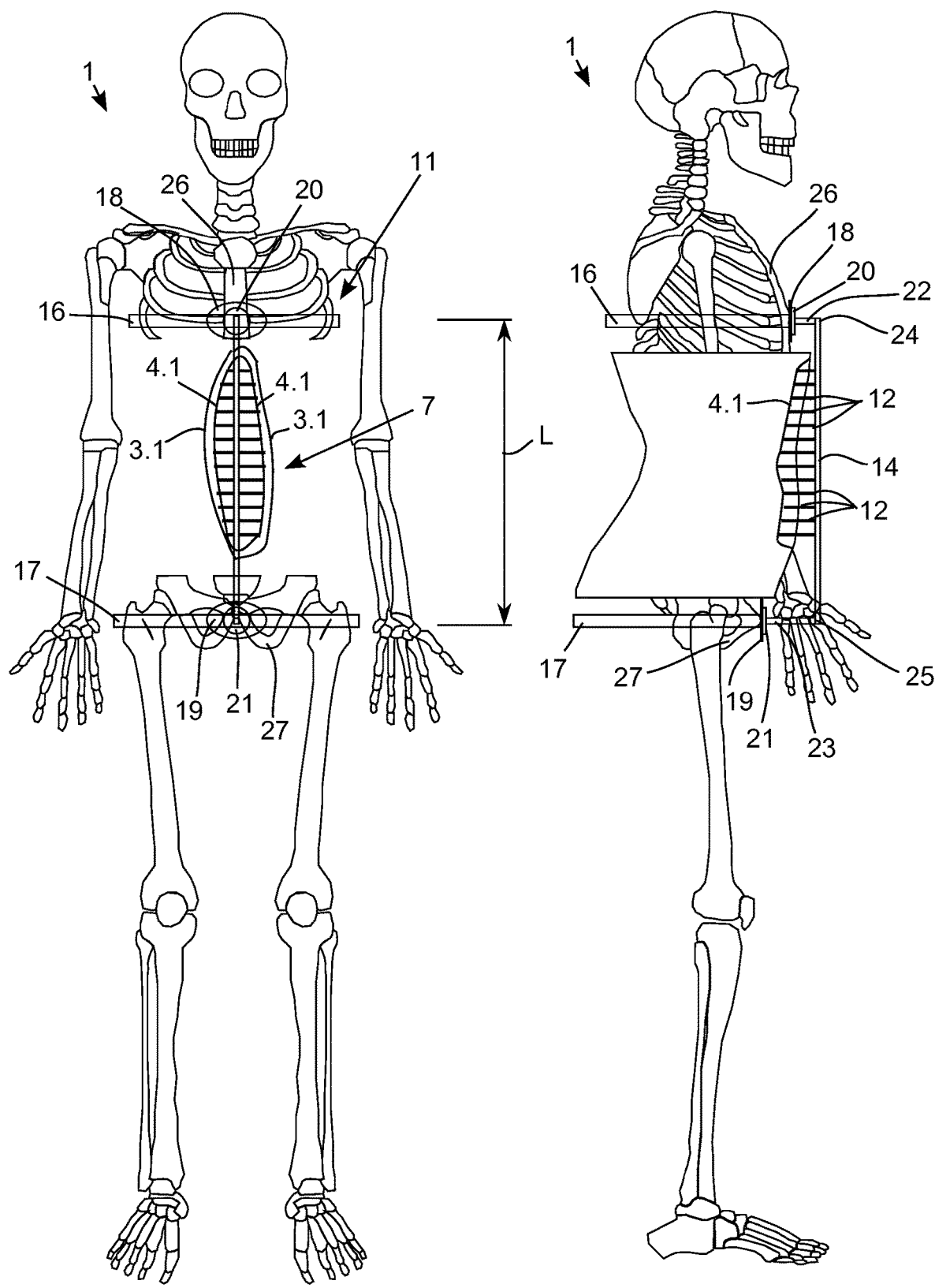
FIG. 5 is a schematic frontal illustration of an open abdomen with an apparatus as per FIG. 3.
FIG. 6 is a schematic sectional illustration of a human abdomen along a sagittal plane with an apparatus as per FIG. 3.
Figure 7:
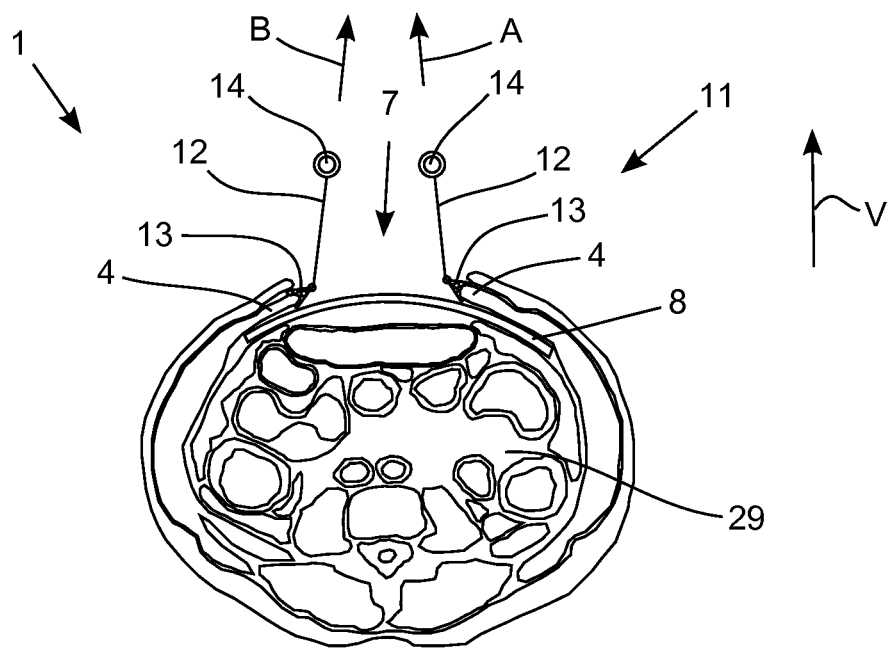
FIG. 7 is a schematic sectional illustration of a human abdomen along a transverse plane with an apparatus according to the invention for reducing the retraction of an opened fascia as per a second exemplary embodiment of the invention.

The tensile elements 12 are connected by way of their respective sides averted from the fascia 4 to a mounting bracket 14. The mounting bracket 14 is arranged outside the body of the patient 1 in the region in front of the opened abdominal wall 2. The mounting bracket 14 is preferably in the form of at least one rod which runs in a vertical direction along the abdominal wall opening 7 and which preferably extends approximately from the region of the sternum 26 to the anterior pelvic ring 27 of the patient 1, cf. FIG. 5 and FIG. 6.

The attachment of the tensile elements 12 to the mounting bracket 14 may be realized by virtue of the tensile elements 12 being led through a passage opening (not illustrated in the figures) in the mounting bracket 14 and then, for example, being knotted. Alternatively, the tensile elements 12 may be attached to the mounting bracket 14 in each case by way of a tensioning apparatus arranged on the mounting bracket 14. The tensioning apparatus may have a force booster. A further alternative attachment of the tensile elements 12 to the mounting bracket 14 may be realized by way of channels arranged on the mounting bracket 14. The tensile elements 12 may advantageously be led through the channels.

As also emerges from the illustrations in FIGS. 3-6, it is possible for all of the tensile elements 12 to be attached to the mounting bracket 14 by way of connecting points which are arranged along a common straight line, whereby a compact construction is made possible. Alternatively, use may be made of a mounting bracket with a curved profile, such that the connecting points are arranged on a curved line, for example a circular line or the circumferential line of a closed curved line, for example of an ellipse.

The mounting bracket 14 is preferably fixed to the body of the patient 1 by way of two fastening devices 16, 17. The fastening devices 16, 17 are in the form of strap-type fasteners which are firmly strapped around the body of the patient 1 in the region of the sternum 26 and in the region of the anterior pelvic ring 27, such that slippage of the fastening devices 16, 17 is as far as possible prevented. The fastening device 17 arranged in the region of the anterior pelvic ring 27 is preferably designed such that, with the fastening device 17 fitted, performing anal hygiene is possible. Here, ventrally, the fastening devices 16, 17 have in each case one pressured-distributing means, for example a support in the form of a gel a plate 18, 19, via which the mounting bracket 14 is supported on the body of the patient 1. Optionally, the pressure-distributing means may have multiple, in particular two, three, four, five or six chambers, which can be selectively filled with a medium such as water, air or gel. On the supports 18, 19 there are arranged in each case holding 20, 21 and a strut 22, 23 extending in a ventral direction. By way of the supports 18, 19, the holding plates 20, 21 and the struts 22, 23, the fastening devices 16, 17 are connected to both ends of the mounting bracket 14.

The fastening devices 16, 17, the struts 22, 23 and the mounting bracket 14 are designed such that they can be adapted to the physical build of the patient 1. The fastening devices 16, 17 may for example be adjustable in length, such that they can be adapted to the circumference of the body of the respective patient 1. The struts 22, 23 are for example of telescopable form, for example in the form of telescopic struts, such that the spacing of the two ends of the mounting bracket 14 from the abdominal wall 2 can be individually adjusted. Furthermore, the mounting bracket 14 is in particular of telescopable form, such that the length of the mounting bracket 14 in a direction running vertically along the abdomen, that is to say in a direction parallel to a connecting line from head to feet, can be adjusted. Alternatively, the struts 22, 23 may be attached displaceably to the mounting bracket 14, such that the spacing of the struts 22, 23 to one another can be adapted to the of the abdominal wall opening 7.

Spring means are preferably provided between the points at which the tensile elements 12 are attached to the mounting bracket 14. In the case of a mounting bracket 14 of telescopable form, for example a telescopic bar, it is preferably the case that resilient telescopic elements are arranged between the points at which the tensile elements 12 are attached to the mounting bracket 14.

The struts 22, 23 are coupled to the mounting bracket 14 in each case by way of a joint 24, 25 which may be in the form of a ball joint or hinge. The mounting bracket 14 is thus mounted so as to be movable relative to the struts 22, 23 and the respective fastening device 16, 17 connected to the struts, such that movements of the patient 1 during respiration or coughing can be compensated. Alternatively, it is possible for selectively only the coupling between the upper fastening device 16 and the mounting bracket 14 or only the coupling between the lower fastening device 17 and the mounting bracket 14 to be realized by way of a joint, and for the respective other coupling of fastening device 16 or 17 and mounting bracket 14 to be of rigid form. As a further alternative, the fastening devices 16, 17 and the mounting bracket 14 may be rigidly coupled. A further alternative provides that the struts 22, 23 are coupled in each case by way of a joint to a fastening device 16, 17 or to a holding plate 20, 21.

As shown in FIG. 3, tensile forces A, B with a force component $A_1$, $B_1$ directed away from the body are generated by way of the apparatus 11. The tensile forces A, B run substantially in a ventrolateral direction, that is to say they are directed laterally forward from the patient. The fascia edges 4.1 are thus held with a spacing to one another which may amount to more than 1 cm, preferably more than 5 cm. At the same time, the fascia edges 4.1 are stretched in a ventral direction V, that is to say in a direction perpendicular to the imaginary connecting line of the fascia edges 4.1, and are prevented from retracting laterally. By contrast to apparatuses which generate only a force component in the direction of the abdominal wall opening 7, it is possible with the apparatus according to the invention for treatment to be performed on the open abdomen. The abdominal cavity 29 is thus enlarged is way of the abdominal wall opening 7 and the ventral displacement of the abdominal wall 2.

When the apparatus 11 is arranged on the body of the patient 1, the abdominal wall opening can be covered by way of sheets. Alternatively, negative-pressure wound therapy may be performed, as will be discussed in more detail below.

Figure 4:
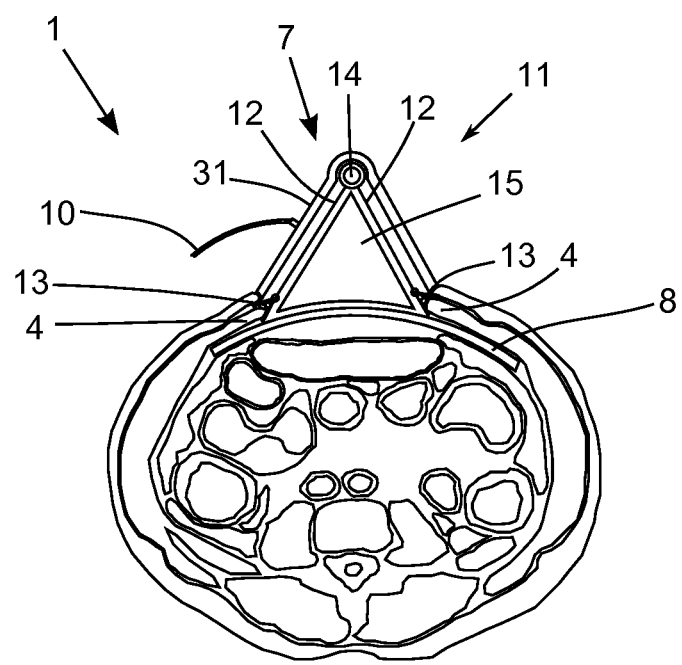
FIG. 4 is a schematic sectional illustration of a human abdomen with a kit according to the invention for treating an open abdomen with an apparatus as per FIG. 3.

The constituent parts of a kit suitable for treatment of the open abdomen are illustrated in FIG. 4. Aside from the above-described apparatus 11 for reducing the retraction of the edges 4.1 of an opened fascia 4, the kit has a sponge 15 which fills the abdominal wall opening 7. The sponge 15 preferably has a substantially triangular cross section such that it fills the region delimited by the tensile elements 12 between the edges 4.1 of the fascia and the mounting bracket 14. The sponge 15 is preferably of dimensionally stable form. The sponge 15 particularly preferably has an internally situated region with increased strength in relation to its surface, or an internally situated, non-deformable basic shape. The tensile elements 12 and the mounting bracket 14 may in particular be covered by a further sponge 31. The sponge 31 is preferably designed so as to be connectable to the tensile elements 12. The sponge 31 may have a section whose shape is adapted to the outer contour of the mounting bracket 14. On the externally situated surface of the sponge 31 there may preferably be arranged, a gas-tight and/or liquid-tight sealing means 30 (not of illustrated in the figures), for example an adhesive film or a gas-tight sleeve. A suction hose 10 may be connected to the sponge 31 such that negative-pressure therapy described above in conjunction with FIG. 2 can be performed.

In a modification of the exemplary embodiment shown in FIGS. 3-6, the tensile elements 12 may preferably have spring means. By way of the spring means, the respective tensile element 12 can be preloaded in the direction of the tensile force A, B and thus held under stress.

The second exemplary embodiment, shown in FIGS. 7-10, of an apparatus 11 for reducing the retraction of the fascia edges 4.1 is substantially identical to the first exemplary embodiment shown in FIGS. 3-6. By contrast to the first exemplary embodiment, multiple mounting brackets 14 are provided in the case of the apparatus 11 as per FIGS. 7-10. The tensile elements 12 connected to a first edge 4.1a of the fascia 4 are connected to a first mounting bracket 14, and the tensile elements 12 connected to a second edge 4.1b of the fascia 4 are connected to a second mounting bracket 4. The mounting brackets 14 are separated from one another by a spacing which corresponds substantially to the spacing of the two fascia edges 4.1a, 4.1b. The tensile forces A, B engage on the fascia 4 in a substantially ventral direction V, that is to say the tensile force is directed forward as viewed from the patient A. In the second exemplary embodiment, the two mounting brackets 14 are arranged parallel. Alternatively, said mounting brackets may be arranged transversely with respect to one another. Through the use of multiple mounting brackets 14, a free space is formed in the region in front of the abdominal wall opening 7, which free space provides easier access to the open abdomen, cf. FIG. 7 and FIG. 9.

Figure 8:
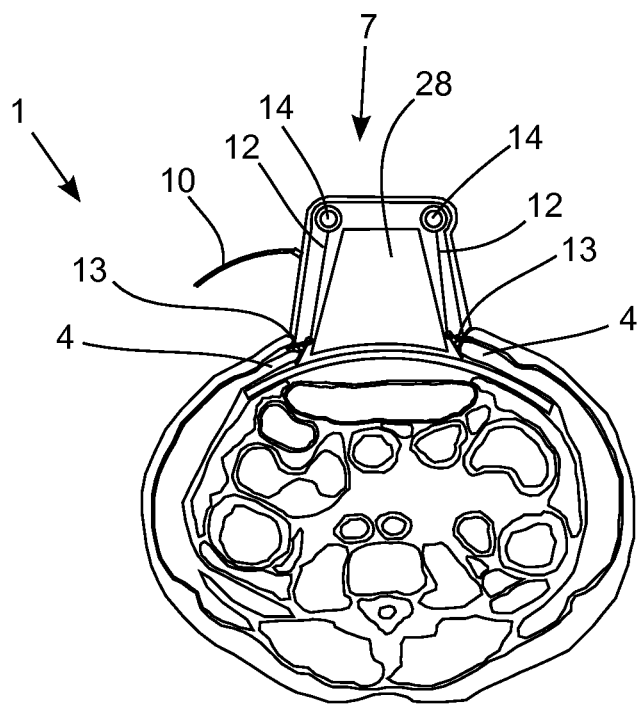
FIG. 8 is a schematic sectional illustration of a human abdomen with a kit according to the invention for treating an open abdomen with an apparatus as per FIG. 7.
Figure 9:
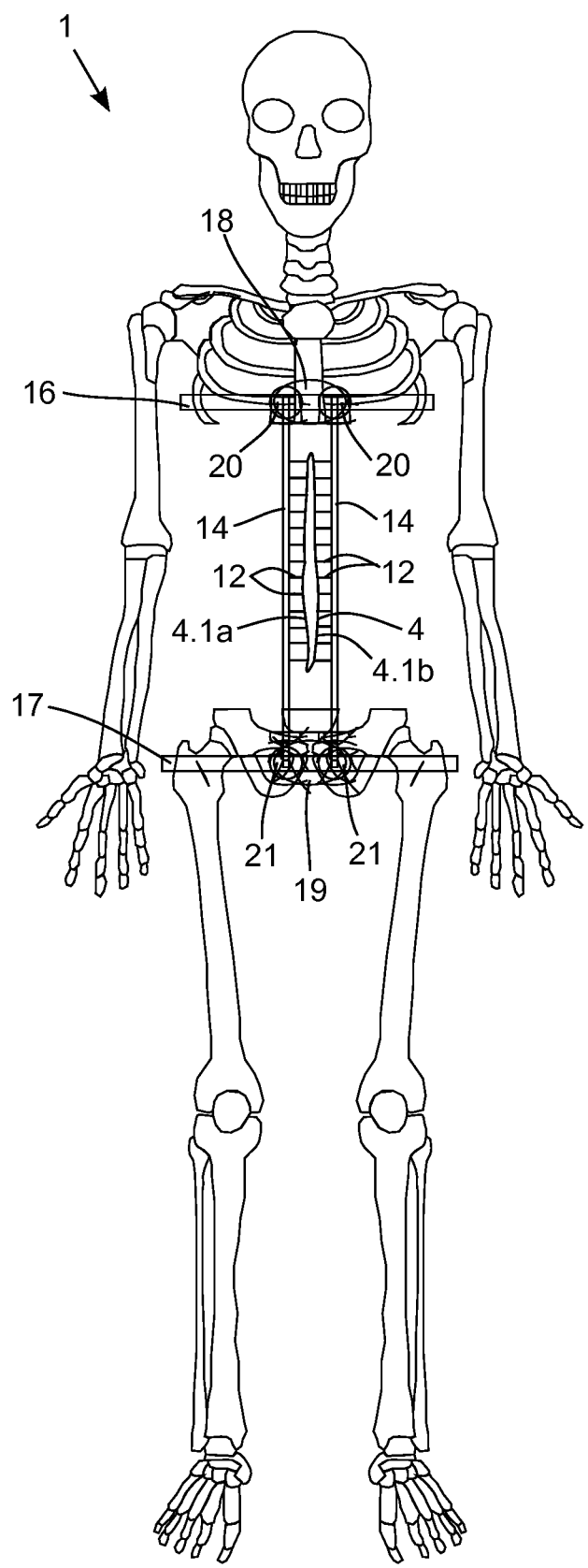
FIG. 9 is a schematic frontal illustration of an open abdomen with an apparatus as per FIG. 7.
Figure 10:
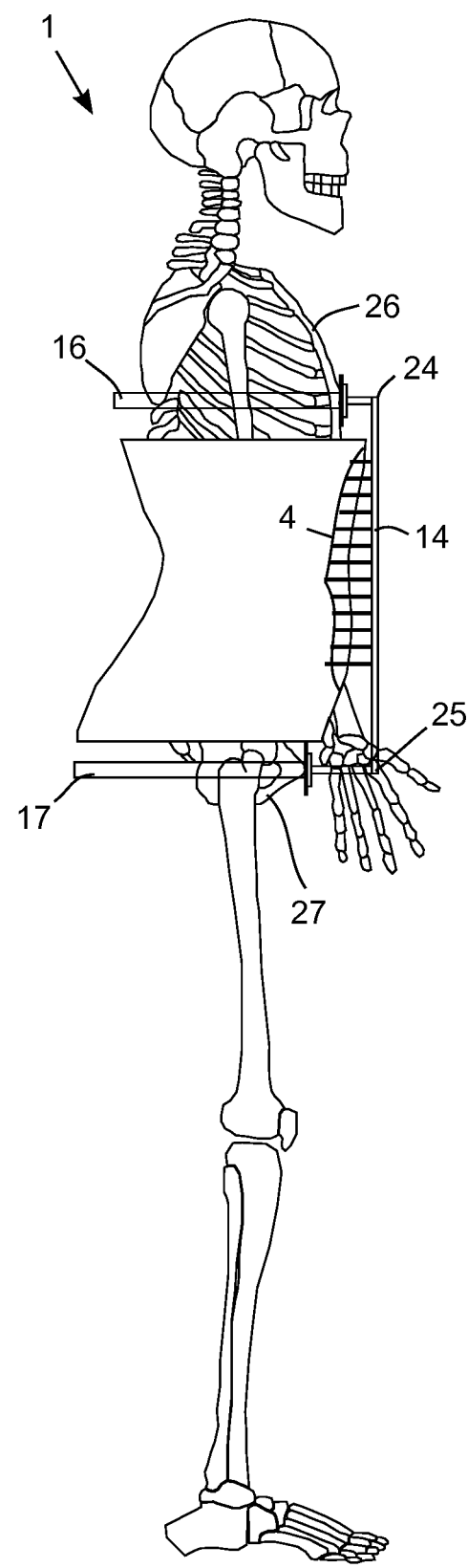
FIG. 10 is a schematic sectional illustration of a human abdomen along a sagittal plane with an apparatus as per FIG. 7.

For the treatment of the open abdomen in the context of negative-pressure therapy, use may be made of a kit having a sponge 28 inserted into the abdominal wall opening 7, which sponge preferably has a rectangular or trapezoidal cross section, cf. FIG. 8. The kit may otherwise be designed in the manner of the kit discussed on the basis of FIG. 4.

In a modification of the second exemplary embodiment, the mounting brackets 14 may be sections of a frame which can be arranged so as to be positioned in front of the abdominal wall opening 7. The frame may have multiple mounting brackets arranged in particular in parallel, which mounting brackets may be arranged along the abdomen in a vertical direction, that is to say parallel to an imaginary line from the head to the feet of the patient 1. The frame may be preferably have multiple sections which are movable relative to one another. For example, the sections of the frame may be connected to one another by way of joints.

Figure 11:
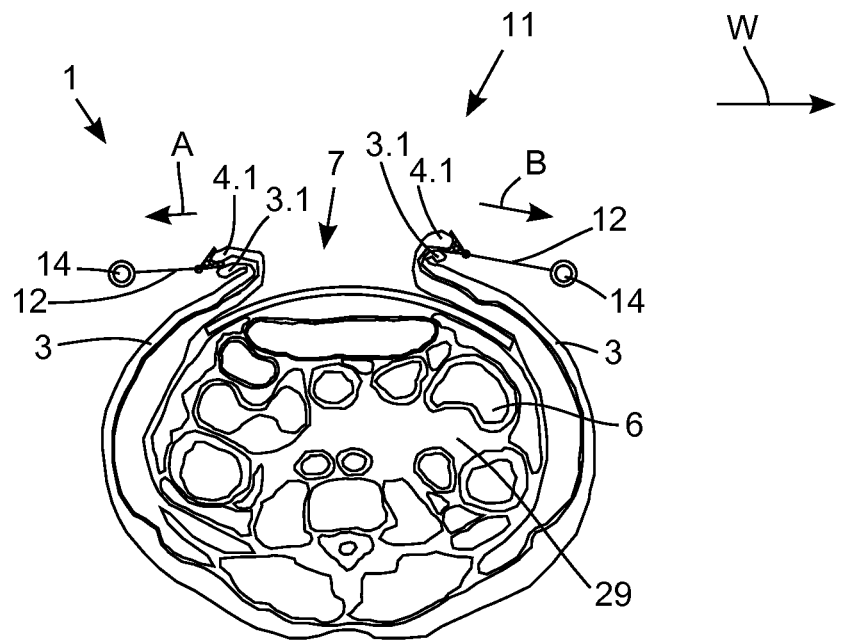
FIG. 11 is a schematic sectional illustration of a human abdomen along a transverse plane with an apparatus according to the invention for reducing the retraction of an opened fascia as per a third exemplary embodiment of the invention.

FIG. 11 illustrates a third exemplary embodiment of the invention. By contrast to the second exemplary embodiment, the spacing between the mounting brackets 14 is greater than the spacing between the edges 4.1 of the fascia 4. In the case of the apparatus 11 as per the third exemplary embodiment, it is the case in particular that tensile forces A, B are exerted on the fascia edges 4.1, which tensile forces have a force component which is directed away from the body and which runs parallel to an imaginary connecting line between the spaced-apart fascia edges 4.1. The tensile forces A, B are in particular directed substantially parallel to the abdominal wall 2 of the patient 1 but away from the abdominal wall opening 7. The tensile forces A, B engage on the fascia 4 substantially in a lateral direction W. The tensile forces A, B engage on the fascia 4 preferably in a direction oriented away from the middle of the abdominal wall opening 7, running parallel to the imaginary connecting line of the fascia edges 4.1. The fascia edges 4.1 are in particular folded over about the skin edges 3.1.

Figure 12:
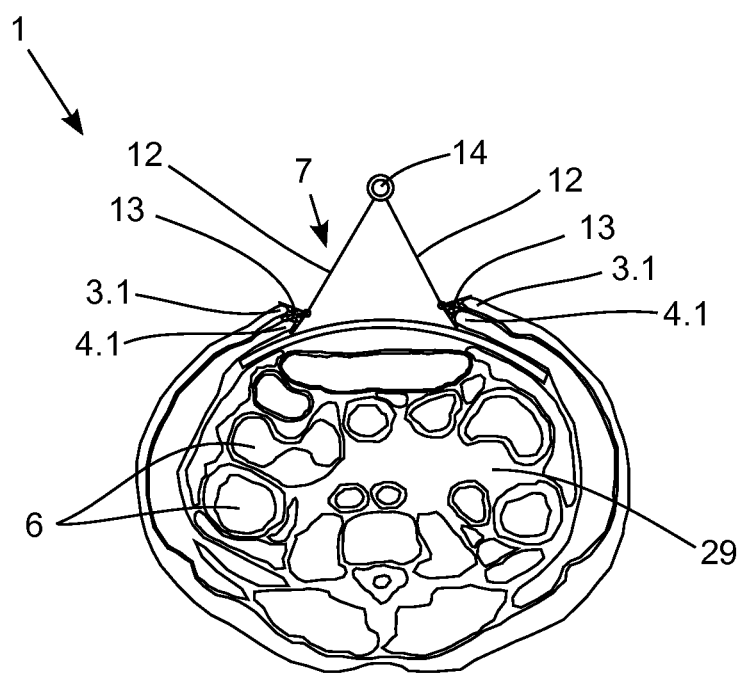
FIG. 12 is a schematic sectional illustration of a human abdomen along a transverse plane with an apparatus according to the invention for reducing the retraction of an opened fascia as per a fourth exemplary embodiment of the invention.

FIG. 12 illustrates a fourth exemplary embodiment of the invention. By contrast to the first exemplary embodiment, the connecting means 13 is connected not only to the fascia edges 4.1 but also to the skin edges 3.1. By way of the apparatus 11 as per FIG. 12, a tensile force. A, B with a force component directed away from the body of the patient 1 can be exerted on the edge 4.1, 3.1 of fascia 4 and skin 3 such that the apparatus 11 holds the edges 4.1, 3.1 of fascia 4 and skin 3 under tension and spaced apart from one another and such that, furthermore, an opened abdominal wall 2 is realized.

Figure 13:
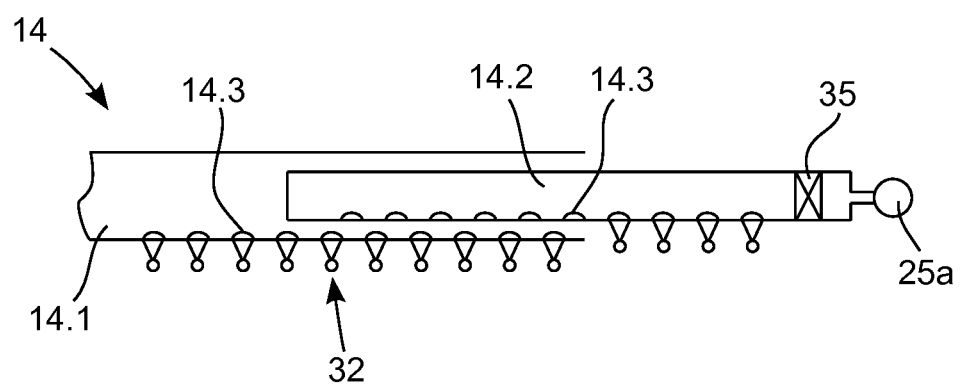
FIG. 13 is a schematic illustration of a mounting bracket.

FIG. 13 shows an example of a mounting bracket 14 such as can be used in an apparatus 11 as per one of the exemplary embodiments described above. The mounting bracket 14 is in the form of a telescopic rod and has at least two parts 14.1 and 14.2 which are movable relative to one another. A first part 14.1 has a larger cross section than a second part 14.2, such that the second part 14.2 can be pushed into the first part 14.1. A joint head 25a ball joint may be integrally formed on or attached to the second part.

The mounting bracket 14, in particular the parts 14.1, 14.2, have multiple connecting points 14.3 by way of which the tensile elements 12 can be attached.

Furthermore, connectors 32 may be provided which are designed such that they can be reversibly attached to the connecting points 14.3. The connecting points 14.3 are preferably in the form of openings. The connectors 32 are preferably designed such that they can be inserted into the openings.

An elastic element 35, for example a spring, is optionally arranged in the region between the connecting points 14.3 and that end of the mounting bracket 14 which is connected to the support 18, 19, in particular that end of the parts 14.1, 14.2. By way of the elastic element 35, movements of those ends of the mounting bracket 14 which are connected to the support 18, 19, in particular as result of respiratory movements or coughing by the patient, can be absorbed. In a modification of the exemplary embodiment as per FIG. 13, an elastic element 35 may be arranged in the region between two connecting points 14.3.

In the illustration in FIG. 13, two parts 14.1 and 14.2 are shown. It is possible for the mounting bracket 14 to be designed so as to have at least three parts, wherein the left-hand part 14.1 shown in FIG. 13 forms a central part with a relatively large cross section, into which the two other parts 14.2 with a relatively small cross section can be pushed. On the central part 14.1 there may be provided a seal such that the length of the mounting bracket 14 can be varied by way of movement of the outer parts 14.2 relative to the central part 14.1, wherein the opened abdomen is sealed off. The seal may for example be formed in the manner of a sealing ring which sealingly surrounds the central part 14.1. The outer parts 14.2 may be situated in a region which is not involved in the sealing of the abdominal cavity the sealing region. The outer parts 14.2 may for example be arranged in front of the pubic region of the patient.

The pubic region is not incorporated into the sealing region for the sealing of the abdominal cavity, because the application of seal elements is impeded there.

In a modification of this exemplary embodiment, a mounting bracket 14 of unipartite form, in particular in the manner of a rod, may be provided, wherein one or more seals are provided on the mounting bracket 14. The seals may be formed in the manner of sealing rings which sealingly surround the mounting bracket 14, in particular the rod.

Figure 14:
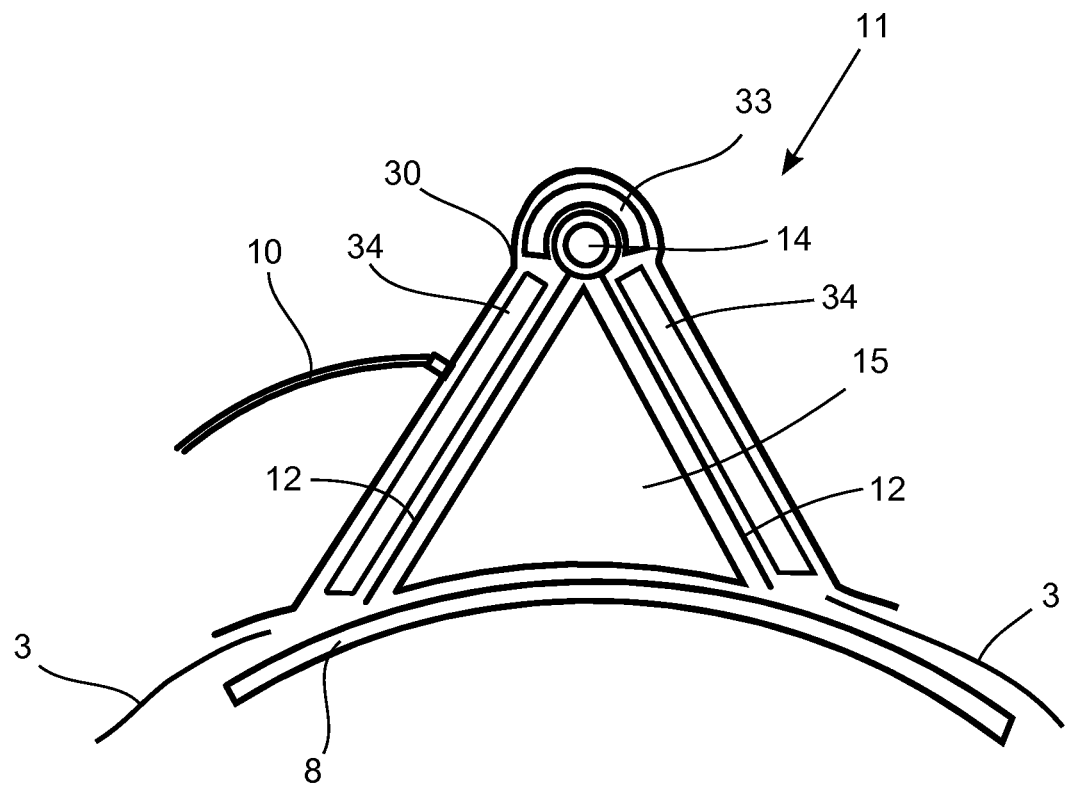
FIG. 14 is a schematic illustration of a human abdomen with a kit according to the invention for treating an open abdomen as per a further exemplary embodiment.

The illustration in FIG. 1A shows a refinement of the kit shown in FIG. 4. By contrast to the kit as per FIG. 4, the kit as per FIG. 14 additionally has a coveting sponge 33, the contour of which is adapted to the outer contour of the mounting bracket 14. Furthermore, two side sponges 34 are provided which can be applied at the outside to the sponge 15 and to the tensile elements 12.

Figure 15A:
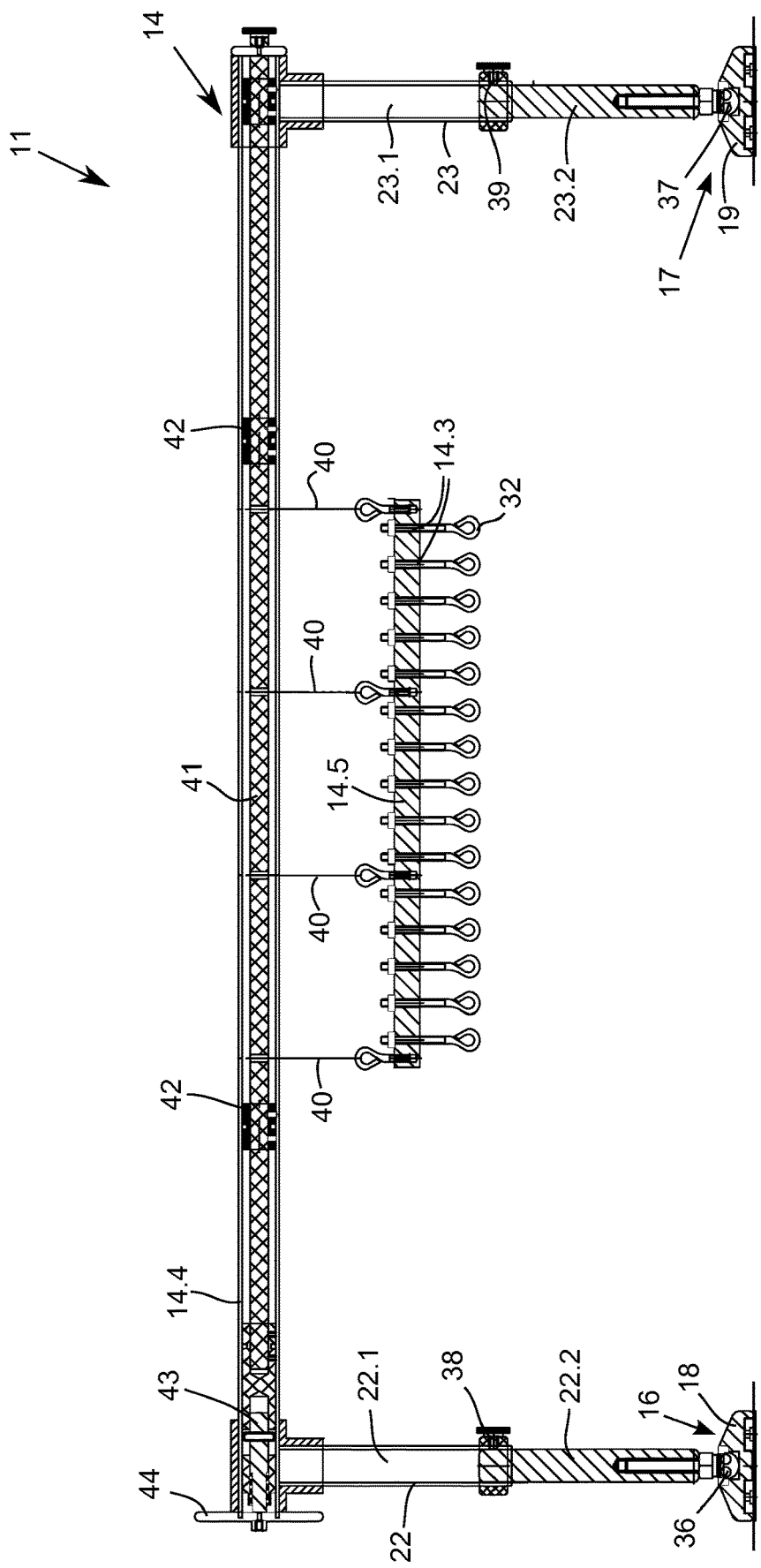
FIG. 15*a* is a schematic sectional illustration of an apparatus for reducing the retraction of an opened fascia as per a fifth exemplary embodiment.
Figure 15B:
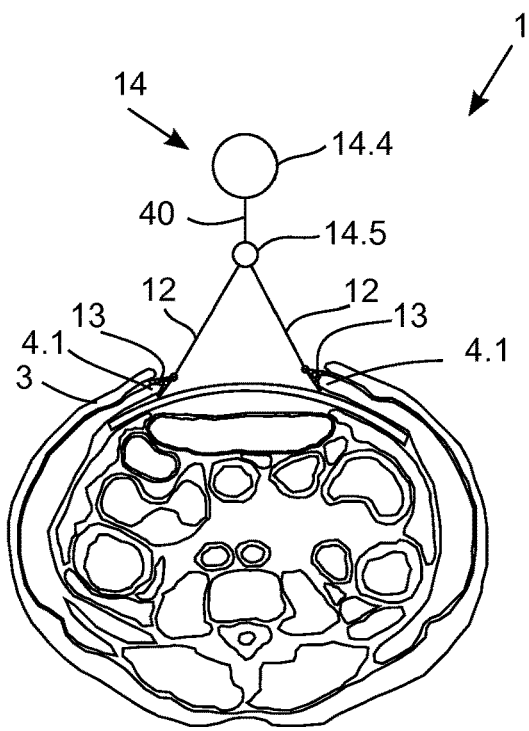
FIG. 15*b* is a schematic sectional illustration of the apparatus from FIG. 15*a;*

FIG. 15a and FIG. 15b show a further exemplary embodiment of an apparatus 11 for preventing the retraction of the fasciae. The apparatus 11 has a mounting bracket 14 via which tensile elements 12 in the form of threads, for example, can be attached. The mounting bracket 14 is rigidly connected to two struts 22, 23, by way of which them mounting bracket 14 can be held in a position spaced apart from the body of the patient 1. The struts 22, 23 are in the form of telescopic struts, such that it is possible for the position of the mounting bracket 14 to be adjusted by way of the struts 22, 23. Furthermore, the struts 22, 23 are displaceable along the mounting bracket 14 and can be selectively fixed at different locations on the mounting bracket 14. It is thus possible for the spacing of the struts 22, 23 to be adapted to the size of the soft tissue defect, for example to the size of the abdominal wall opening. The struts 22, 23 connect the mounting bracket 14 in each case to a fastening device 16, 17 which lies on the skin 3 of the patient 1.

The struts 22, 23 have in each case two strut elements 2.1, 22.2, 23.1 23.2 which are, movable relative to one another. On the struts 22, 23 there is provided in each case one fixing apparatus 38, 39, by way of which the strut elements 22.1, 22.2, 23.1, 23.2 can be fixed relative to one another. The fixing apparatus 38, 39 may for example be formed in the manner of a fixing screw.

The struts 22, 23 preferably have a force measurement device (not shown in the figures) by way of which the sum of the tensile force imparted by the tensile elements can be measured. Alternatively, a force measurement device may be provided as part of the fastening device 16, 17.

The apparatus 11 is designed such that the tensile force engages on the fascia 4 in a direction which encloses an angle which lies in the range from 5° to 90°, or in the range from 10° to 80°, or in the range from 15° to 70°, with a virtual connecting line between the edges 4.1 of the opened fascia 4. The angle preferably lies in the range from 30° to 60°, particularly preferably in the range from 35° to 55°. For example, the angle may amount to substantially 45°. In relation to the longitudinal axis of a strut 22, 23, the tensile force engages on the fascia 4 in a direction which encloses an angle which lies in the range from 0° to 85°, or in the range from 10° to 80°, or in the range from 20° to 75°, with the longitudinal axis of the strut 22, 23. The angle preferably lies in the range from 30° to 60°, particularly preferably in the range from 35° to 55°. For example, the angle may amount to substantially 45°.

On a side averted from the mounting bracket 14, the struts 22, 23 have in each case one joint 36, 37 by way of which the struts 22, 23 are connected to a support 16, 19 of a fastening device 16, 17. The fastening device 16, 17 may furthermore have one or more straps for the fixing of the supports 18, 19 to the patient 1. The joint 36, 37 is preferably in the form of a ball joint. When the apparatus 11 is arranged on the body of a patient 1, the supports 18, 19 of the fastening devices 16, 17 are supported on the skin of the patient 1, preferably in a region of the skin in which no tensile forces are exerted by the apparatus 11 on the fascia lying under the skin.

Alternatively, the fastening devices 16, 17 may have a connecting region by way of which the fastening devices 16, 17 can be fastened to a bone of the patient 1.

The mounting bracket 14 of the apparatus 11 has a two-part construction, which will be described in more detail below. The mounting bracket 14 has a holding element 14.4, which is in particular connected rigidly to the struts 22, 23, and an attachment element 14.5, which is movable relative to the holding element 14.4. On the attachment, element 14.5 there are provided multiple connecting points 14.3 by way of which tensile elements 12 can be attached. The connecting points 14.3 are for example in the form of bores. Connectors 32, which are in particular in the form of eyebolts, are arranged in the connecting points 14.3. Alternatively, the connectors may be in the form of detent elements with eyelets, which can be inserted into the connecting points 14.3 and locked with detent action in the connecting points. The position of the connectors 32 relative to the attachment element 14.5 is adjustable, such that, by way of the adjustment of the position of the connectors 32, the tension of the tensile elements 12 can be adjusted independently of one another. The connectors 32 thus form a tensioning device by way of which the tension of the tensile elements 12 can be individually adjusted. The attachment element 14.5 is connected by way of multiple cables 40 or chains to the holding element 14.4, wherein a first end of a cable 40 or a chain is fixedly fastened to the attachment element 14.5. A second end of the cable 40 or of the chain is connected to a shaft 41 mounted in the holding element 14.4 such that the cable 40 or the chain can be wound up when the shaft 41 is rotated. By way of the rotation of the shaft 41, the position of the attachment element 14.5, and thus the tension of all of the tensile elements 12 attached to the attachment element 14.5, can be adjusted jointly. In this respect, groupwise adjustment of the tension of the tensile elements 12, or adjustment of the spacing between the holding element 14.4 and the attachment element 14.5, is made possible by way of the rotation of the shaft 41. The shaft 41 is connected by way of a fixing coupling 43 to an actuating element 44. The fixing coupling 43 is designed so as to normally block a rotation of the shaft 41 and to permit a rotation of the shaft 41 only when the actuating element 44 is pulled out of the mounting bracket 14, in particular out of the holding element 14.4, in the direction of the axis of rotation of the shaft 41.

The attachment element 4.5 is exchangeable either separately from or together with the shaft 41 or a part of the shaft 41. The connectors 32 may be exchanged together with the attachment element 14.5. A disposable attachment element is thus provided.

If the apparatus 11 is used in the context of negative-pressure wound therapy, the mounting bracket 14 of the apparatus 11 may be arranged such that the mounting bracket 14 is situated in the region that is sealed off in gas-tight fashion. To permit re-tensioning of the tensile elements 12 even in the case of an applied negative-pressure wound bandage, the mounting bracket may be arranged such that the actuating element 42 is arranged outside the region that is sealed off in gas-tight fashion. To prevent an ingress of air through the mounting bracket 14 into the region that is sealed off in gas-tight fashion, the mounting bracket 14 preferably has a housing that is sealed off in gas-tight fashion. For example, the holding element 14.4 may have one or more seals 42 which seal off the shaft 42 with respect to the holding element 14.4. For sealing purposes, a non-adhesive, air-impermeable film is used. The film has two openings through which the mounting bracket 14, in particular the holding element 14.4, is guided. The film is sealed off with respect to the mounting bracket 14, in particular the holding element 14.4, by way of sealing means.

Figure 15C:
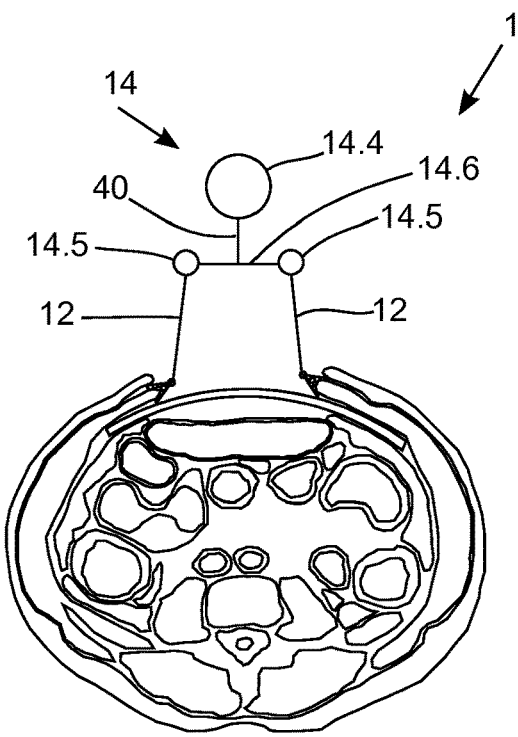
FIG. 15*c* is a schematic sectional illustration of a modification of the apparatus from FIG. 15*a;*
Figure 16:
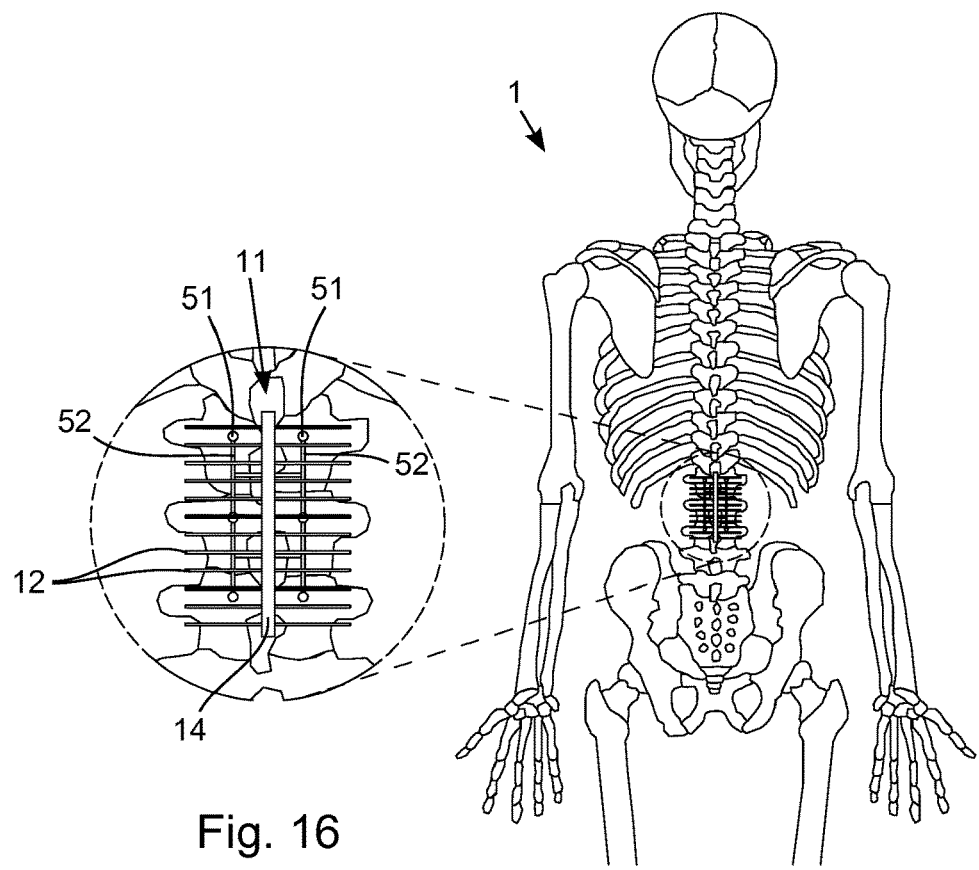
FIG. 16 is a schematic illustration of an open back wall defect with an apparatus for reducing the retraction of an opened fascia.
Figure 17:
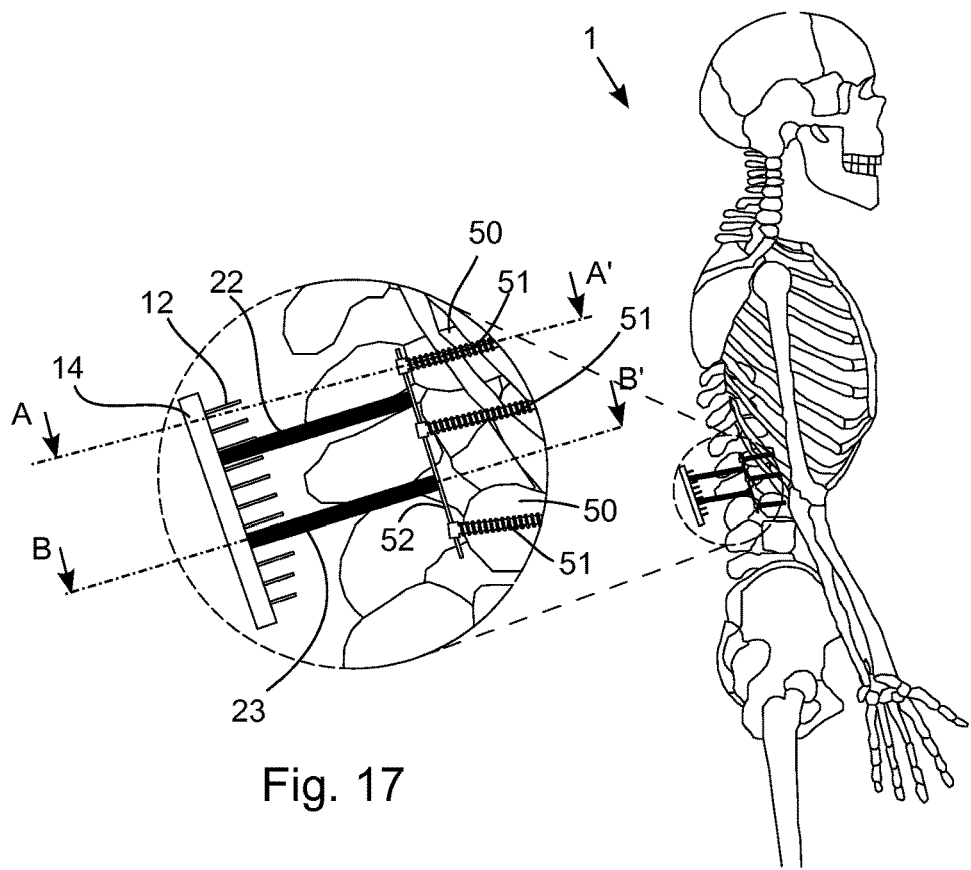
FIG. 17 is a schematic sectional illustration of an open back wall defect along a sagittal plane with an apparatus as per FIG. 16.
Figure 18:
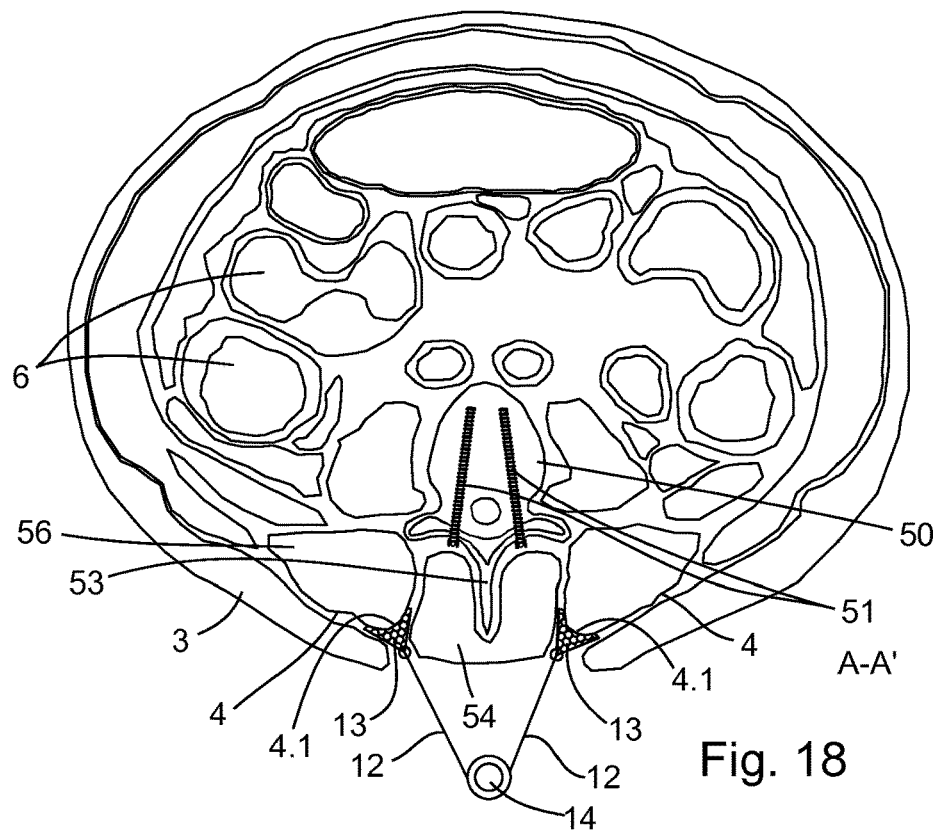
FIG. 18 is a schematic sectional illustration of a human torso along the transverse plane A-A' from FIG. 17.
Figure 19:
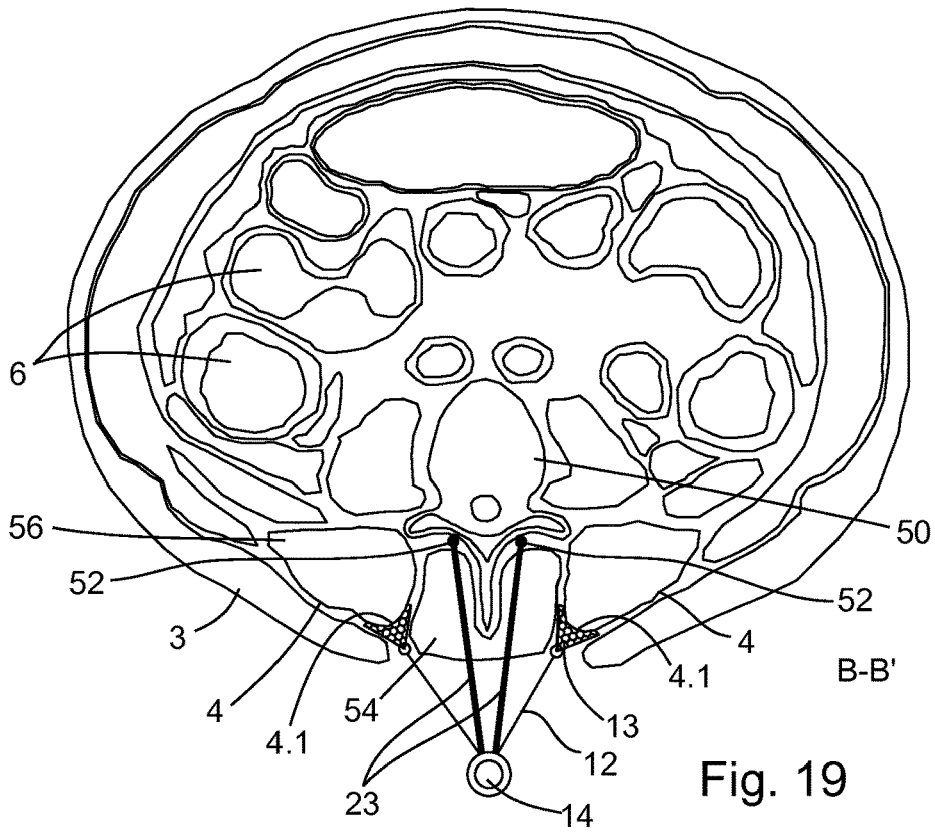
FIG. 19 is a schematic sectional illustration of a human torso along the transverse plane B-B' from FIG. 17.

FIG. 15c shows a modification of the exemplary embodiment shown in FIG. 15a and FIG. 15b, in which the mounting bracket 14 has a holding element 14.4 and multiple, in particular two, attachment elements 14.5 that are movable relative to the holding element 14.4. The attachment elements 14.5 are connected to one another by way of a spacer element 14.6. The spacing of the attachment elements 14.5 to one another is adjustable. For the adjustment of the spacing, the spacer element 14.6 may be of telescopable form.

Below, on the basis of the illustrations in FIGS. 16-21, it is sought to describe an exemplary embodiment of an apparatus 11 according to the invention which is suitable for the treatment of an open back wall. The opening of the back wall may be necessary for example for the treatment of vertebral fractures, of spondylolisthesis, of vertebral disk damage, of constrictions of the spinal canal, of infections or tumors on the spinal column, and of dysplasia and malpositioning of the spinal column. In particular in the event of infections occurring after operations have taken place, it is sometimes possible for the back wall to be left open for the purposes of infection treatment. To counteract the occurrence of infections and facilitate the care of the open back wall, the back wall defect is generally temporarily sealed off. Negative-pressure wound therapy may optionally be performed.

In the region of the back, a fascia 4 encloses the back muscle 56 that lies under the skin 3.

The apparatus 11 for preventing the retraction of the fasciae 4 has a mounting bracket 14 which is formed in the manner of a rod and which is connected to struts 22, 23. The struts 22, 23 connect the mounting bracket 14 to a fastening device which is in the form of an implant already arranged in the body of the patient, that is to say as an internal fixator. The implant is composed of multiple, in particular two, longitudinal bars 52 which are fixed to the pedicle screws 51 by way of grub screws (not shown in the figures). The pedicle screws 51 extend through the pedicle of the vertebra 50 and extend into the region of the vertebral body of the vertebra 50. The implant has multiple longitudinal rods 52 which are in each case connected to the pedicle screws 51 in two or more vertebrae 50 and which fix the position of said vertebrae 50 relative to one another.

Tensile elements 12 may be attached to the mounting bracket 14, by way of which tensile elements tensile forces can be exerted on the fascia edges 4.1. Said tensile elements 12 are preferably in the form of threads, wires, cables or meshes. The tensile elements 12 may be of elastic or non-elastic form. It is basically possible for the tensile elements 12 to be connected directly to the fascia 4. To prevent the tensile elements 12 from being torn out, and to prevent damage to the fascia 4, the tensile elements 12 are preferably connected to the fascia by way of an areal connecting means 13 in the form of a mesh.

As can be seen from the illustrations in FIGS. 18-21, the mounting bracket 14 is arranged outside the body of the patient 1 with a certain spacing to the open defect in the skin 3. In a modification of the exemplary embodiment, it is possible for the mounting bracket 14 to be arranged in the plane of the skin defect or to the inside of the plane of the skin defect but outside the plane of the fascia defect. In a further modification, the apparatus according to this exemplary embodiment may have multiple mounting brackets 14. It is for example possible for the tensile elements 12 to be attached to multiple mounting brackets 14 which are in the form of rods running substantially parallel, as has been described above in conjunction with the illustrations in FIGS. 7 and 8 with regard to use in the region of the abdomen.

Figure 20:
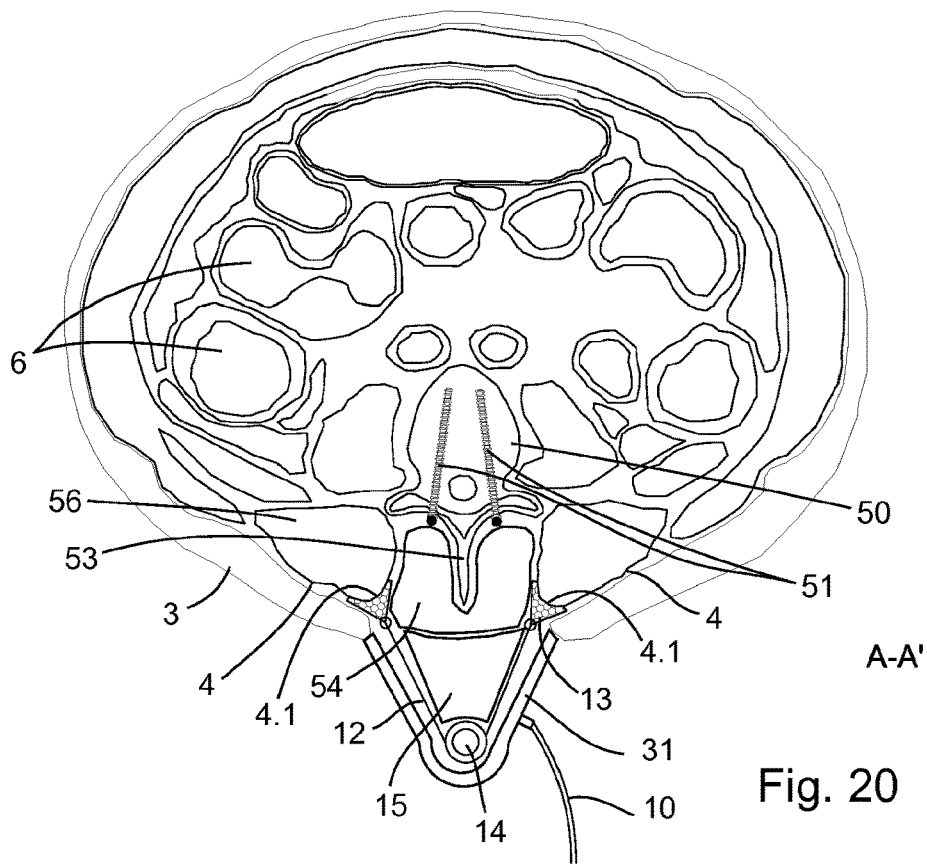
FIG. 20 is a schematic sectional illustration of a human torso along the transverse plane A-A' from FIG. 17 with a kit according to the invention for treating an open back.
Figure 21:
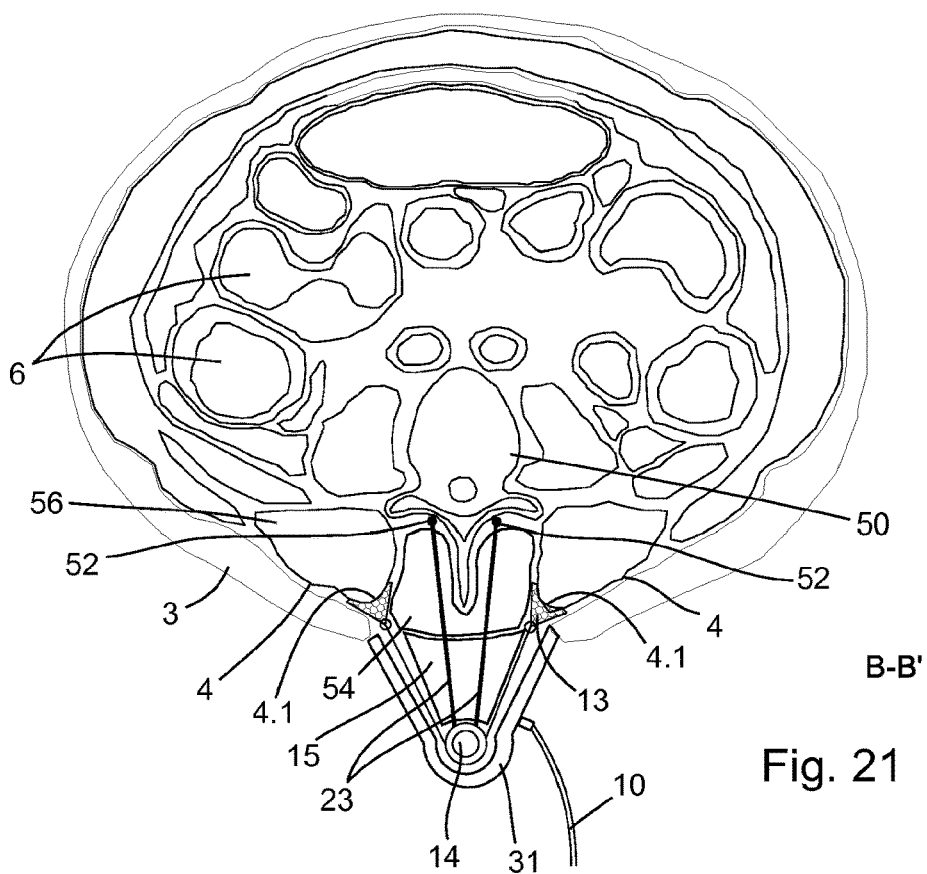
FIG. 21 is a schematic sectional illustration of a human torso along the transverse plane B-B' from FIG. 17 with a kit according to the invention for treating an open back with an apparatus as per FIG. 16.

The illustrations in FIGS. 20 and 21 show the constituent parts of a kit for treating an open skin defect in the form of an open back wall. The kit has not only the above-described apparatus 11 for reducing the retraction of the edges 4.1 of an opened fascia 4 but also a first sponge 54 which is adapted to the contour of the vertebra 50 such that the spinous process 53 of the vertebra 50 engages into a recess of the sponge 54. Furthermore, the first sponge 54 has openings through which the struts 22, 23 of the apparatus 11 can be guided. Furthermore, a second sponge 15 is part of the kit, wherein the second sponge 15 fills the skin defect. The second sponge preferably has a substantially triangular cross section such that it fills the region delimited by the tensile elements 12 between the edges 4 of the fascia and the mounting bracket. The sponge 15 is preferably of dimensionally stable form. The sponge 15 particularly preferably has an internally situated region with increased strength in relation to its surface, or an internally situated, non-deformable basic shape. The tensile elements 12 and the mounting brace 14 may in particular be covered by a third sponge 31. The third sponge 31 is preferably designed to be connectable to the tensile elements 12. The third sponge 31 may have a section whose shape is adapted to the outer contour of the mounting bracket 14. On the externally situated surface of the third sponge 31 there may preferably be arranged a gas-tight and/or liquid-tight sealing means (not illustrated in the figures), for example an adhesive film or a non-adhesive film that is impermeable to air. A suction hose 10 may be attached to the third sponge 31, such that negative-pressure therapy as described above in conjunction with FIG. 2 can be performed.

Figure 22:
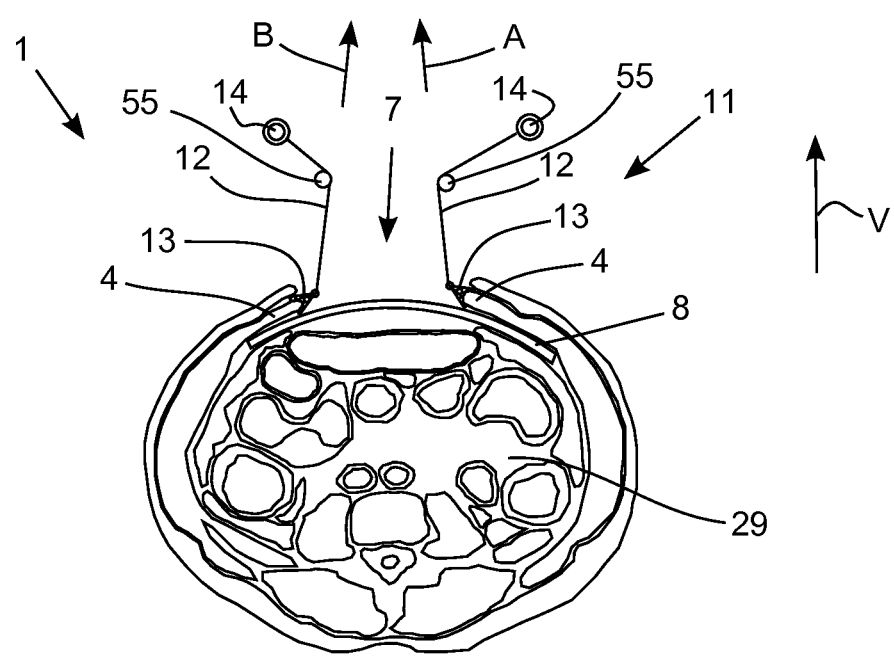
FIG. 22 shows a modification of the exemplary embodiment shown in FIG. 7 with a diverting device.

In the case of the above-described apparatuses 11 for reducing the retraction of the edges 4.1 of a fascia 4, it is optionally possible for a diverting device 55 for the diversion of the tensile elements 12 to be provided. A diverting device of said type is shown by way of example in FIG. 22. The diverting device is formed in the manner of a rod around which the tensile element 12 is guided. The tensile element 12 thus runs from the fascia 4 over the diverting device 55 to the mounting bracket 14.

The above-described kits for treating an open soft tissue defect, in particular an open abdominal wall 2 or an open soft tissue defect on the back, having at least one sponge 15, 28 for filling a soft tissue defect, in particular an abdominal wall opening or an open soft tissue defect on the back, each have an apparatus 11 for reducing the retraction of the edges of an opened fascia 4 of a patient 1 with an open soft tissue defect, in particular with an open abdominal wall 2 or an open soft tissue defect on the back, by way of which apparatus a tensile force with a force component $A_1$, $B_1$ directed away from the body of the patient can be exerted on the edges of the fascia 4 such that the apparatus 11 holds the edges of the fascia 4 under tension and spaced apart from one another and such that an open soft tissue defect, in particular an opened abdominal wall or an open soft tissue defect on the back, remains present.

By way of the apparatus 11 according to the invention, the fascia 4 can be held open to such an extent that the body cavity, in particular the abdominal cavity 29 or the cavity situated to the inside of the back wall, is freely accessible, and/or the internal organs 6 can emerge at least substantially unhindered through the open soft tissue defect, in particular the abdominal wall opening 7 or an open soft tissue defect on the back. Furthermore, the apparatus 11 may be used to stretch a fascia 4 whose edges 4.1 have already retracted. The apparatus according to the invention may be used without negative-pressure wound therapy being performed.

LIST OF REFERENCE DESIGNATIONS

1 Patient
2 Abdominal wall
3 Skin
3.1 Skin edge
4 Fascia
4.1 Fascia edge
4.1*a*, 4.1*b* Fascia edge
5 Abdominal muscle
6 Intestine
7 Abdominal wall opening
8, 9 Sponge
10 Suction hose
11 Apparatus for reducing the retraction of the fascia
12 Tensile element
13 Connecting means
14 Mounting bracket
14.1, 14.2 Parts
14.3 Connecting point 14.4 Holding element
14.5 Attachment element
14.6 Spacer element
15 Sponge
16, 17 Fastening device
18, 19 Support
20, 21 Holding plate
22, 23 Strut
22.1, 22.2 Strut element
23.1, 23.2 Strut element
24, 25 Joint
25a Joint head
26 Sternum
27 Anterior pelvic ring
28 Sponge
29 Abdominal cavity
30 Sealing means
31 Sponge
32 Connector
33 Covering sponge
34 Side sponge
35 Elastic element
36, 37 Joint
38, 39 Fixing apparatus
40 Cable
41 Shaft
42 Seal
43 Fixing coupling
44 Actuating element
50 Vertebra
51 Pedicle screw
52 Longitudinal bar
53 Spinous process
54 Sponge
55 Diverting device
56 Back muscle
A, B Tensile force
$A_1, B_1, A_2, B_2$ Force component
L Length
V Ventral direction
W Lateral direction

The invention claimed is:

1. An apparatus for reducing a retraction of edges of an open fascia of a patient with an open soft tissue defect, by way of which apparatus a tensile force with a force component directed away from a body of a patient can be exerted on the edges of the fascia such that the apparatus holds the edges of the fascia under tension and spaced apart from one another and such that the open soft tissue defect, in particular an opened abdominal wall or an open soft tissue defect on a back, remains present; wherein the apparatus further includes:
   at least one tensile element that can be connected to the fascia;
   a mounting bracket, which can be arranged outside the body of the patient in front of the soft tissue defect and to which the at least one tensile element can be attached, wherein the mounting bracket is attachable to a holder which is independent of the patient; and
   a force measurement device for measuring a tensile force exerted on the fascia by the at least one tensile element.

2. The apparatus as claimed in claim 1, wherein the tensile force engages on the fascia substantially in a ventral direction or in a ventrolateral direction or in a lateral direction or in a dorsal direction or in a dorsolateral direction.

3. The apparatus as claimed in claim 1, wherein the at least one tensile element is in a form of a thread and/or in a form of a wire and/or in a form of a mesh.

4. The apparatus as claimed in claim 1, wherein the at least one tensile element has a spring means.

5. The apparatus as claimed in claim 1, wherein the at least one tensile element can be connected to the fascia, or to an entire soft tissue mantle, directly or by way of a connecting means of areal form.

6. The apparatus as claimed in claim 1, wherein the tensile force can be adjusted by way of a tensioning apparatus arranged on the mounting bracket, which tensioning apparatus has a force booster.

7. The apparatus as claimed in claim 1, wherein the mounting bracket can be arranged so as to run vertically along an abdomen or vertically along the back.

8. The apparatus as claimed in claim 1, wherein the mounting bracket is coupled to a fastening device by way of at least one joint.

9. The apparatus as claimed in claim 1, wherein a length of the mounting bracket can be adjusted in a direction running vertically along an abdomen.

10. The apparatus as claimed in claim 1, wherein the holder that is independent of the patient is in a form of a boom extension or a bed mounting point attached to a bed or a holder that is supported on a ground.

11. The apparatus as claimed in claim 1, wherein the mounting bracket comprises one or more rods.

12. The apparatus as claimed in claim 1, wherein the apparatus comprises various tensile elements that can be connected to the fascia, wherein the force measurement device is designed such that a sum of the tensile forces exerted by the various tensile elements can be measured.

13. The apparatus as claimed in claim 1, wherein the force measurement device comprises a spring force sensor or an inductive force sensor or a capacitive force sensor or an optical force sensor or a strain gauge or a magnetic force sensor or an electromagnetic force sensor or a piezoelectric force sensor.

14. A kit for treating an open soft tissue defect having at least one sponge for filling the open soft tissue defect, comprising the apparatus for reducing the retraction of the edges of the open fascia of the patient as claimed in claim 1.

15. The kit as claimed in claim 14, wherein the kit has a sponge, a contour of which is adapted to an outer contour of the mounting bracket.

16. The kit as claimed in claim 14, wherein the kit has a sealing means for sealing off the open soft tissue defect, which sealing means is in a form of a non-adhesive film that is impermeable to air.

17. A method for reducing a retraction of edges of an open fascia of a patient with an open soft tissue defect;
   wherein a tensile force with a force component directed away from a body of the patient is exerted on the edges of the fascia such that the edges of the fascia are held under tension and spaced apart from one another and such that the open soft tissue defect, in particular an opened abdominal wall or an open soft tissue defect on a back, remains present;
   wherein at least one tensile element is connected to the fascia;
   wherein a mounting bracket is arranged outside the body of the patient in front of the soft tissue defect and the at least one tensile element is attached to the mounting bracket;

wherein the mounting bracket is attached to a holder which is independent of the patient; and wherein a force measurement device measures a tensile force exerted on the fascia by the at least one tensile element.

\* \* \* \* \*